(12) United States Patent
Hwang et al.

(10) Patent No.: US 7,960,130 B2
(45) Date of Patent: Jun. 14, 2011

(54) METHOD FOR ACTIVATION OF TRANSIENT RECEPTOR POTENTIAL CATION CHANNEL, SUBFAMILY A, MEMBER 1 USING ACETALDEHYDE

(75) Inventors: Sun Wook Hwang, Seoul (KR); Sang Su Bang, Gwangmyeong-si (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 148 days.

(21) Appl. No.: 12/109,256

(22) Filed: Apr. 24, 2008

(65) Prior Publication Data

US 2009/0269280 A1    Oct. 29, 2009

(51) Int. Cl.
G01N 33/567 (2006.01)
G01N 33/52 (2006.01)
G01N 33/88 (2006.01)
C12N 5/0793 (2010.01)

(52) U.S. Cl. .......................... 435/7.21; 435/325; 436/501

(58) Field of Classification Search .......................... None
See application file for complete search history.

(56) References Cited

OTHER PUBLICATIONS

Fang CX et al. Acetaldehyde promotes rapamycin-dependent activation of p70-S6K and glucose uptake despite inhibition of Akt and mTOR in dopaminergic SH-SY5Y human neuroblastoma cells. Exp Neurol. 2007; 203:196-204.*
Jordt SE et al. Mustard oils and cannabinoids excite sensory nerve fibers through the TRP channel ANKTM1. Nature, 2004; 427(6971):260-265.*
Story GM et al. ANKTM1, a TRP-like channel expressed in nociceptive neurons, is activated by cold temperatures. Cell, Mar. 21, 2003; 112(6):819-829.*
Bradley DM et al. In vitro comparison of the effects of ethanol and acetaldehyde on dorsal root ganglion neurons. Alcohol Clin Exp Res. 1995; 19(5):1345-1350.*
Andrade E.L. et al., (Apr. 25, 2006). Contractile mechanisms coupled to TRPA1 receptor activation in rat urinary bladder. Biochem Pharmacol. 72(1): 104-114.
Bandell M. et al., (Mar. 2004). Noxious cold ion channel TRPA1 is activated by pungent compounds and bradykinin. Neuron. 41(6): 849-857.
Bang S. et al., (Apr. 26, 2007). Transient receptor potential A1 mediates acetaldehyde-evoked pain sensation. The 15th Meeting of Korean Basic Medical Scientists.
Bang S. et al., (Oct. 23, 2007). Transient receptor potential A1 mediates acetaldehyde-evoked pain sensation. Eur. J. Neurosci. 26(9): 2516-23.
Namer B. et al., (Jun. 2005). TRPA1 and TRPM8 activation in humans: effects of cinnamaldehyde and menthol. Neuroreport. 16(9):955-959.
Trevisani M. et al., (Aug. 7, 2007). 4-Hydroxynonenal, an endogenous aldehyde, causes pain and neurogenic inflamation through activation of the irritant receptor TRPA1. Proc. Natl. Acad. Sci. U.S.A. 104(33):13519-13524.

* cited by examiner

*Primary Examiner* — Elizabeth C. Kemmerer
*Assistant Examiner* — Kimberly A. Ballard
(74) *Attorney, Agent, or Firm* — Greenlee Sullivan P.C.

(57) ABSTRACT

The present invention relates to a method for activation of TRPA1 (transient receptor potential cation channel, subfamily A, member 1) using acetaldehyde, more precisely a method for selecting a candidate for TRPA1 activation blocker from neurons activated by acetaldehyde. Acetaldehyde of the present invention works on TRPA1 specifically so that it facilitates the isolation of sensory neurons expressing TRPA1. Therefore, acetaldehyde of the invention can be effectively used for the studies on TRPA1 mechanisms and the development of a TRPA1 based anodyne.

10 Claims, 17 Drawing Sheets

[Fig. 1a]
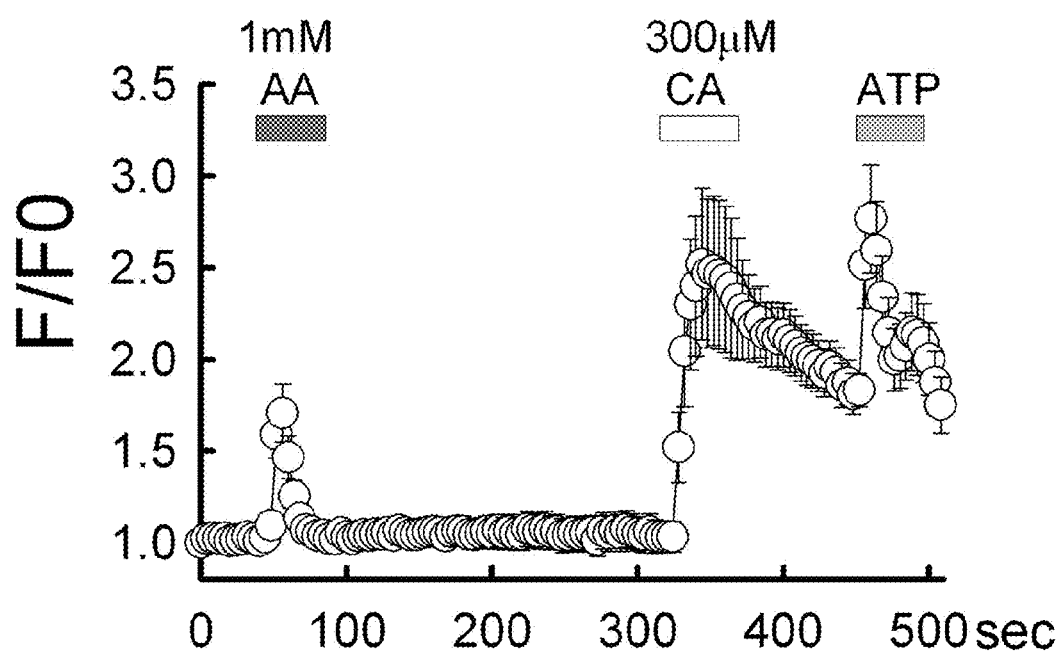

[Fig. 1b]
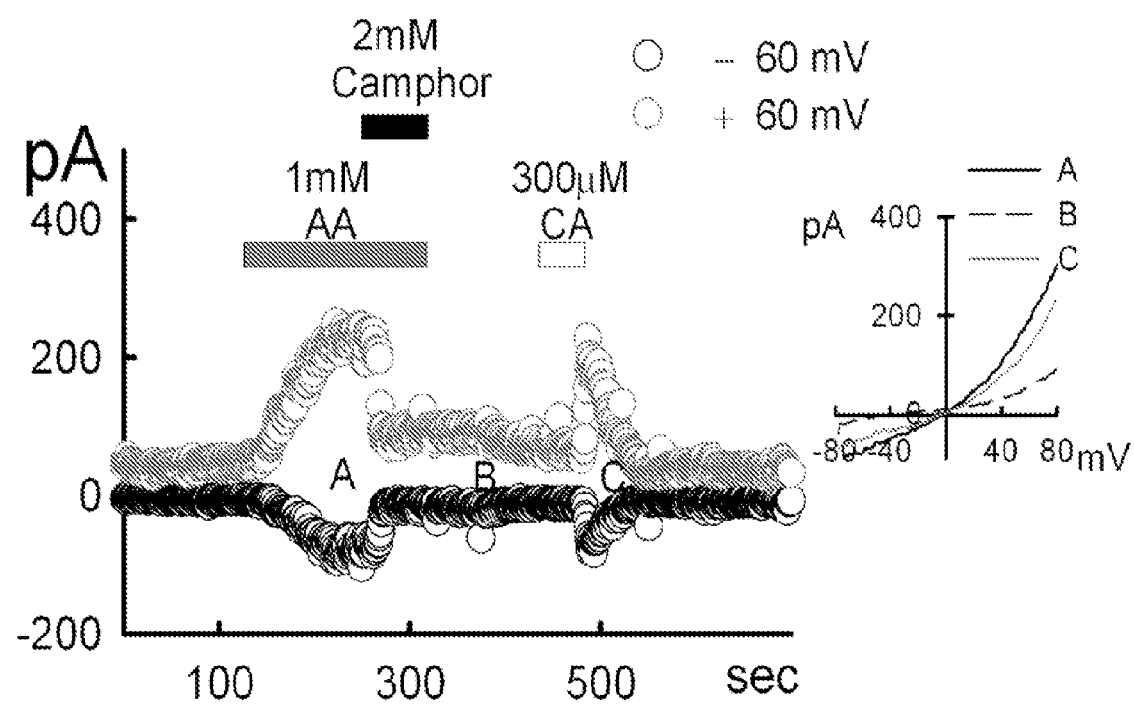

[Fig. 1c]
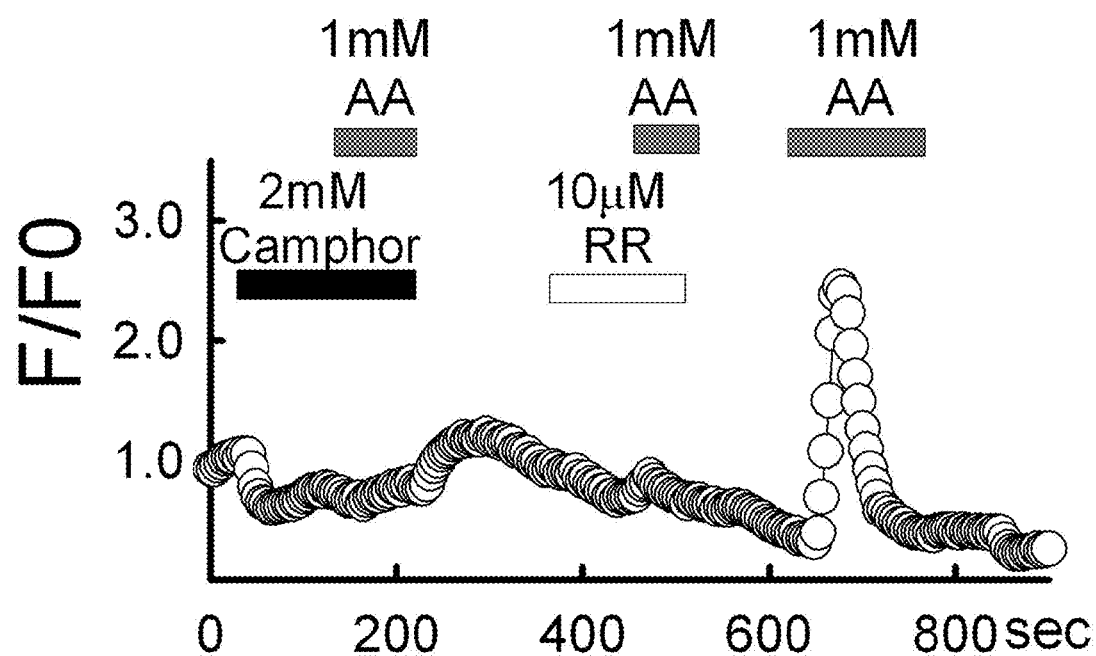

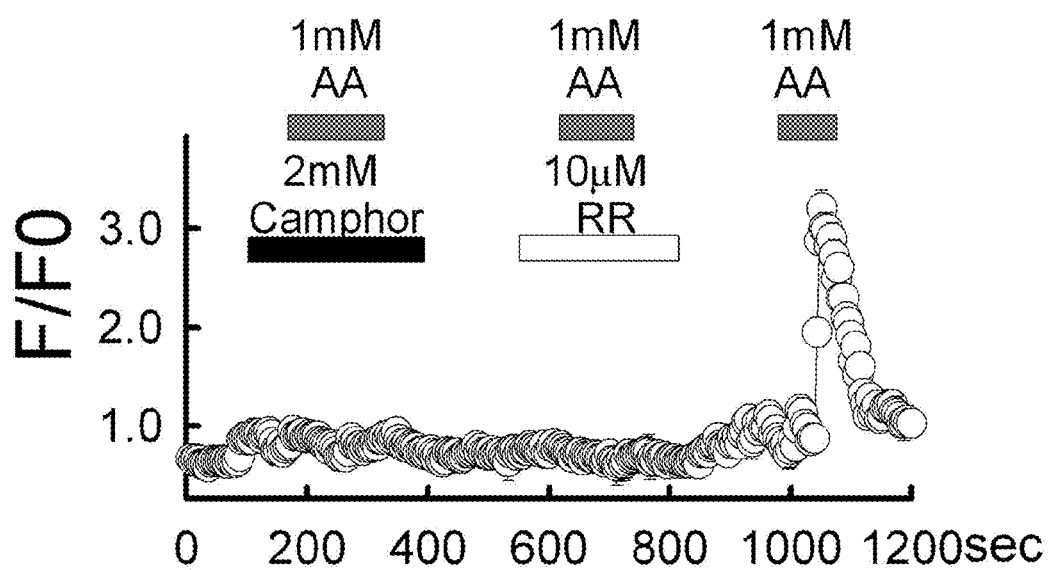
[Fig. 1d]

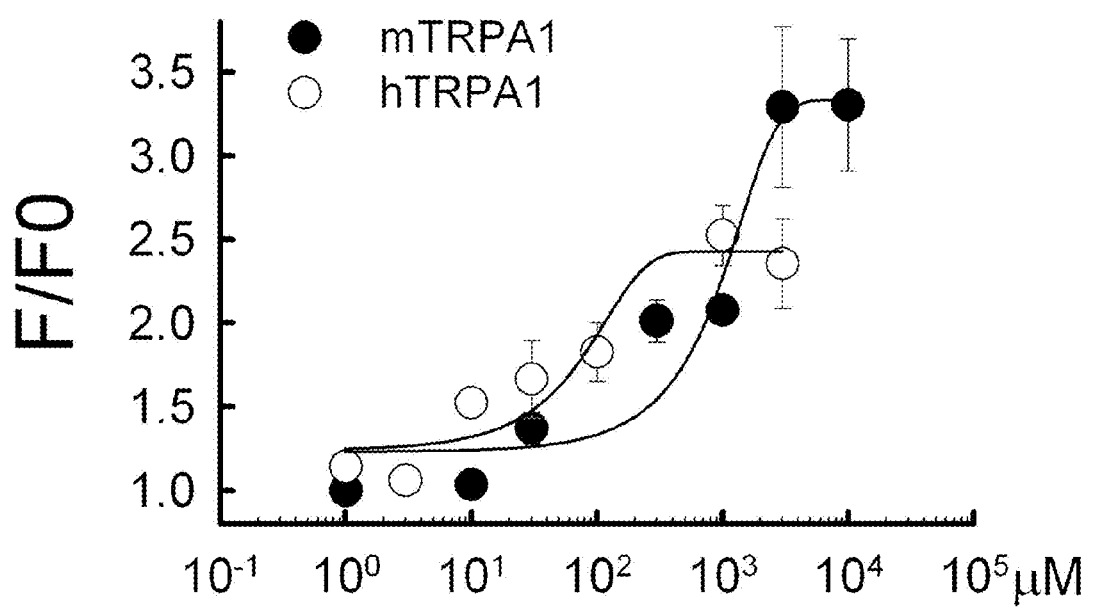
[Fig. 2a]

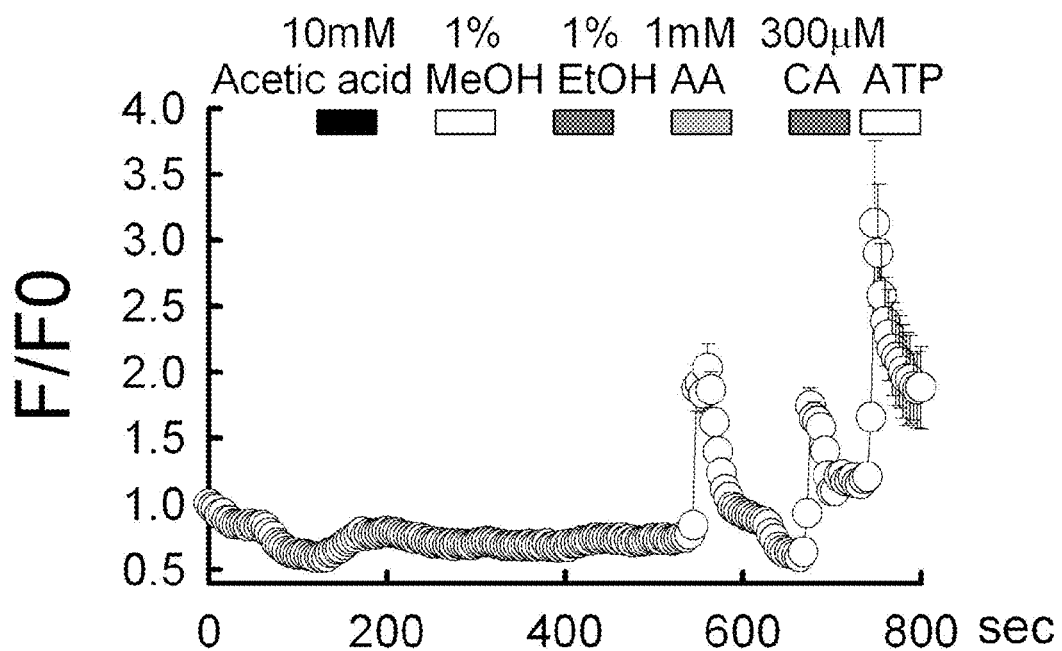
[Fig. 2b]

[Fig. 2c]
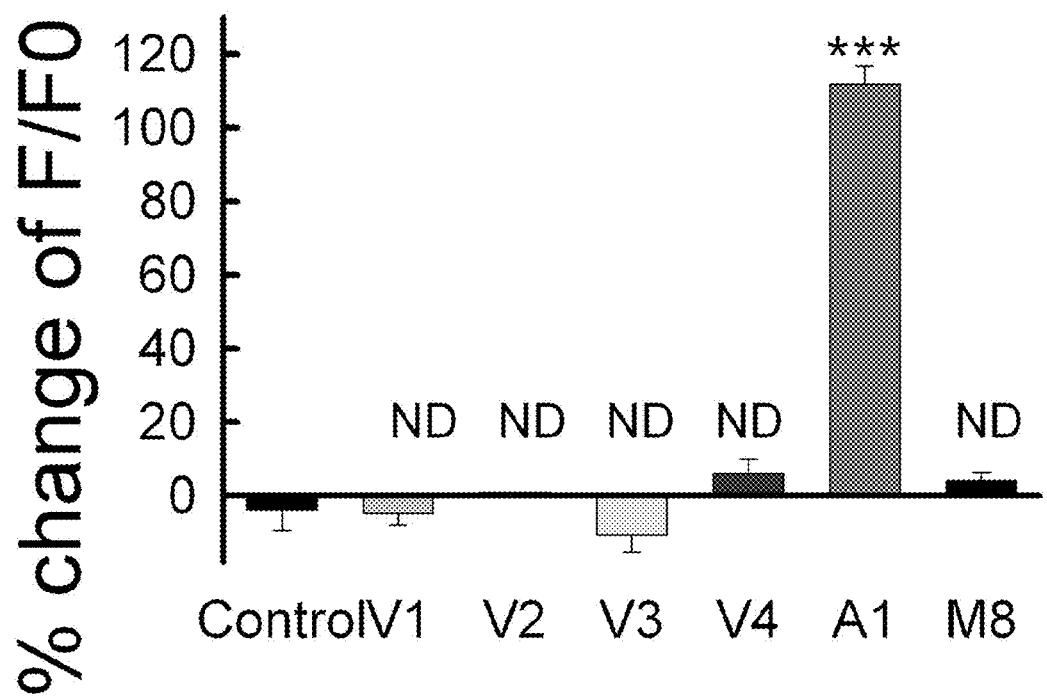

[Fig. 2d]
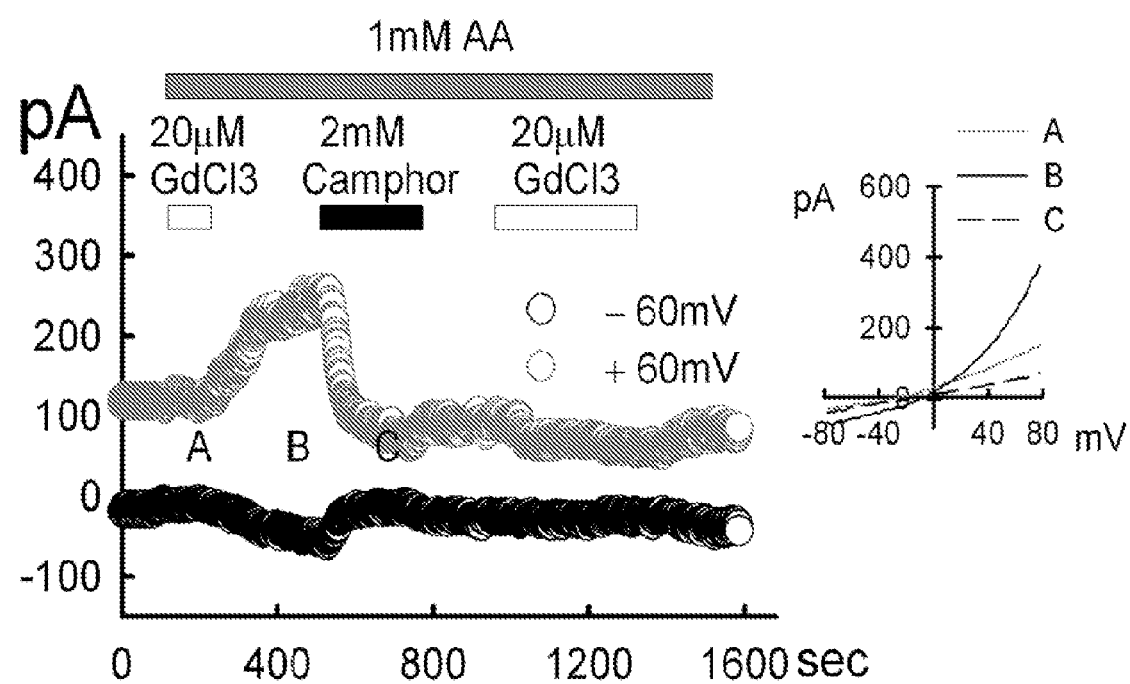

[Fig. 3a]
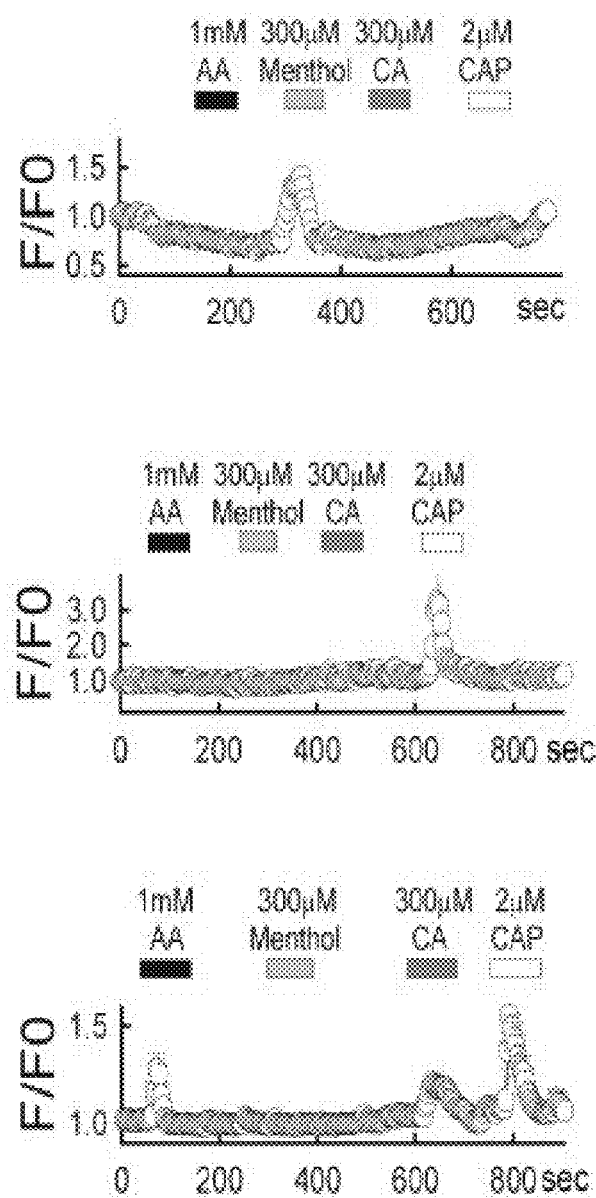

[Fig. 3b]
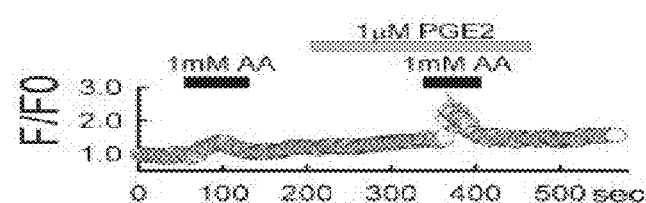

[Fig. 3c]
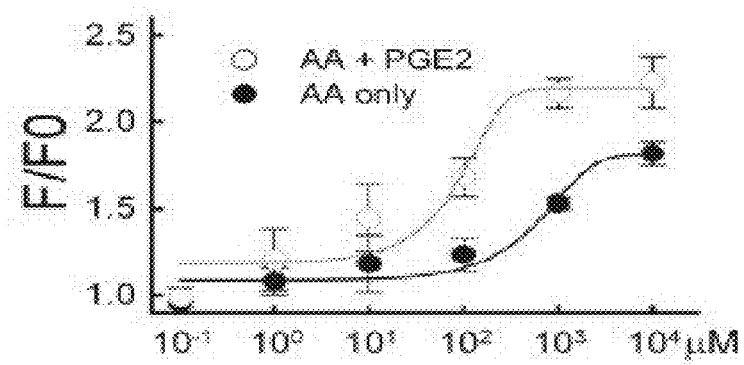

[Fig. 3d]
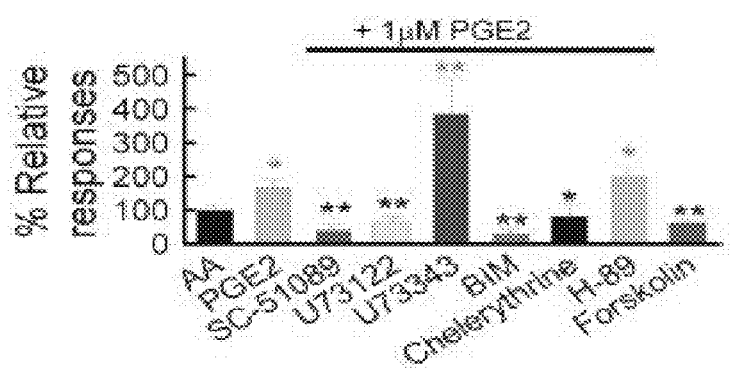

[Fig. 4a]
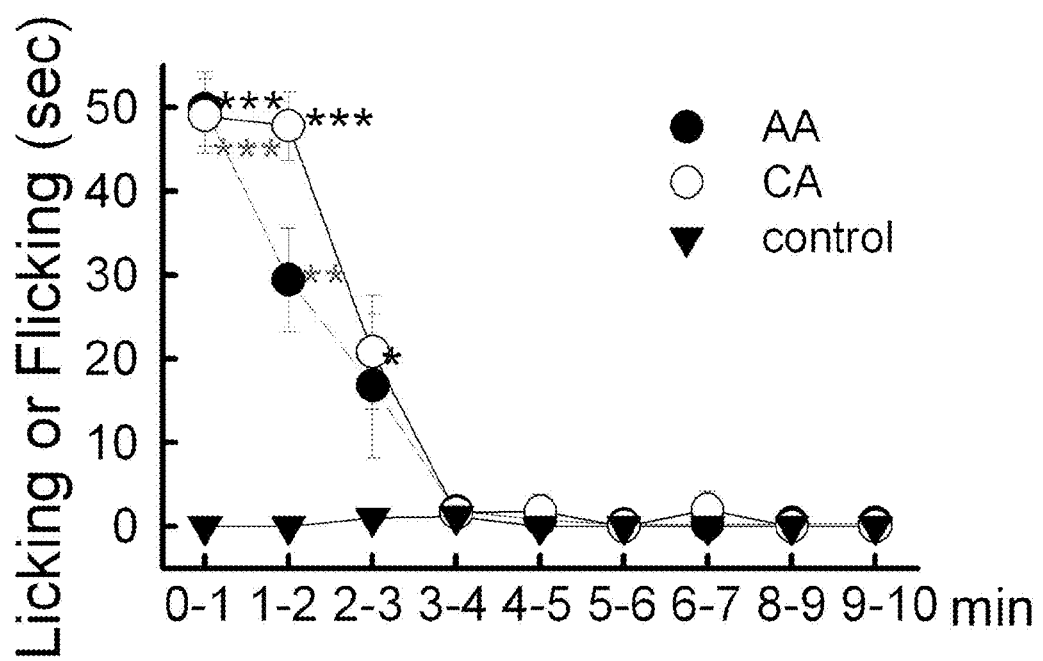

[Fig. 4b]
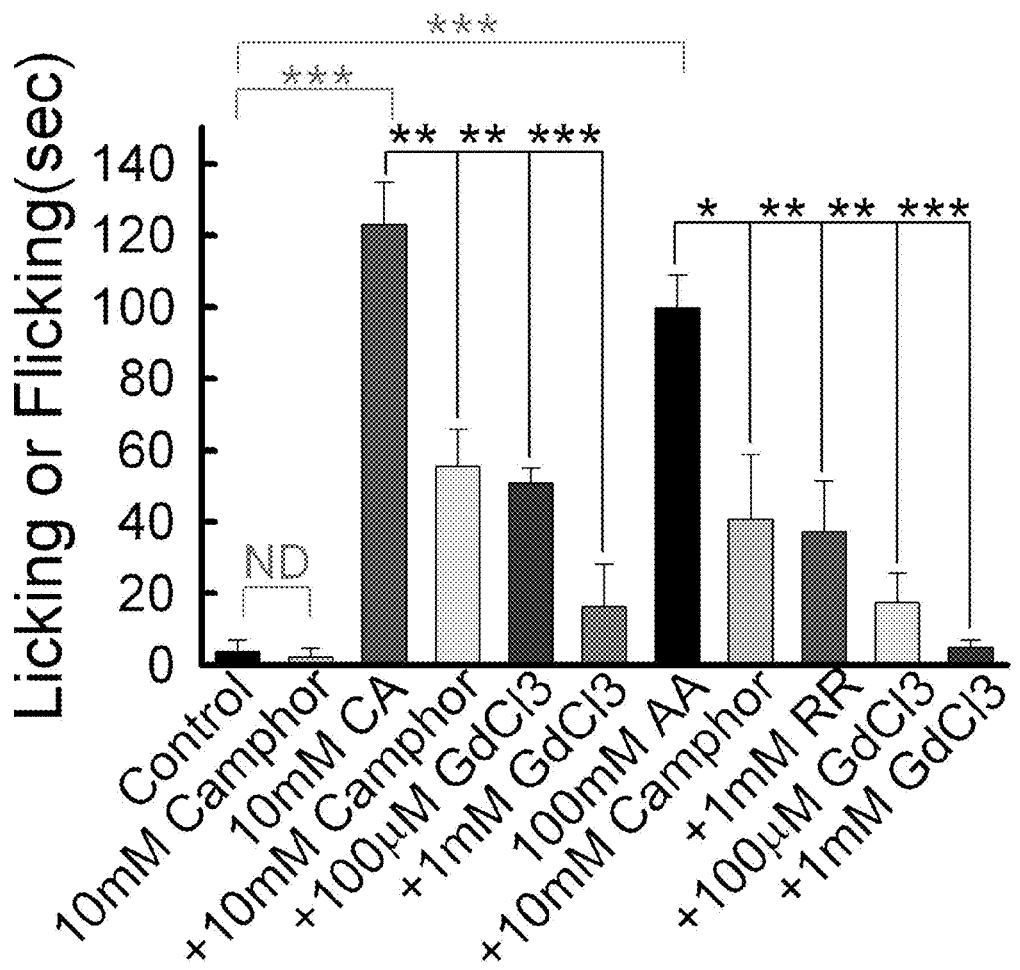

[Fig. 4c]
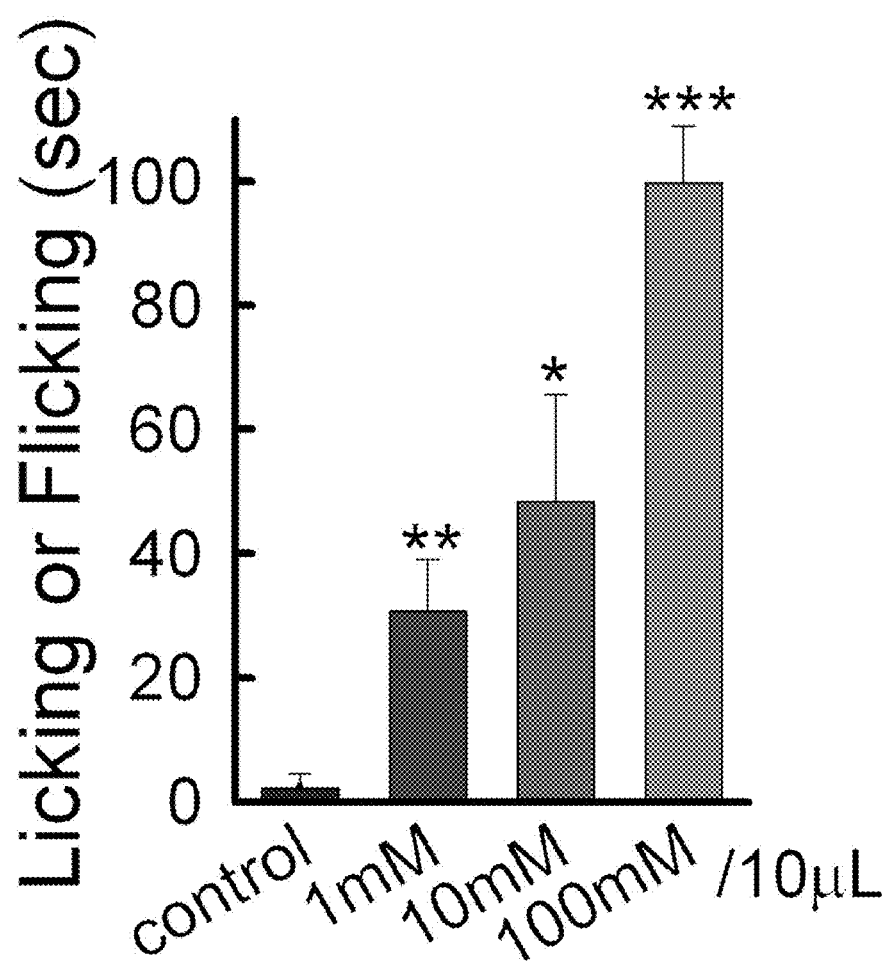

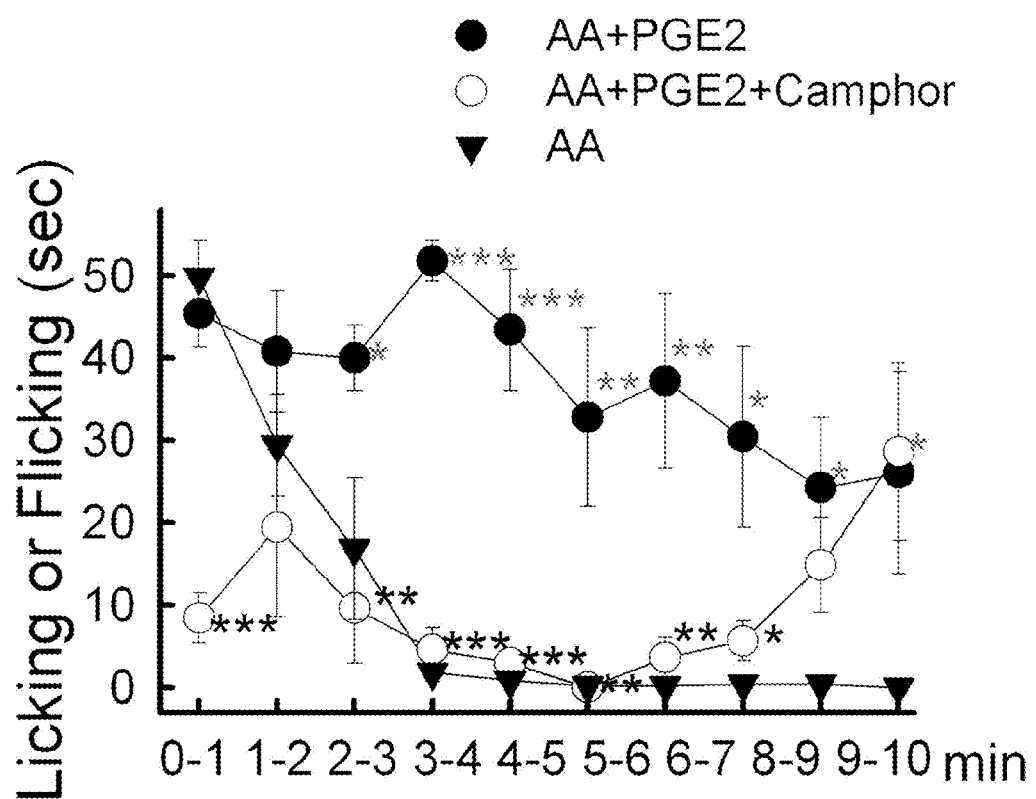
[Fig. 4d]

[Fig. 4e]
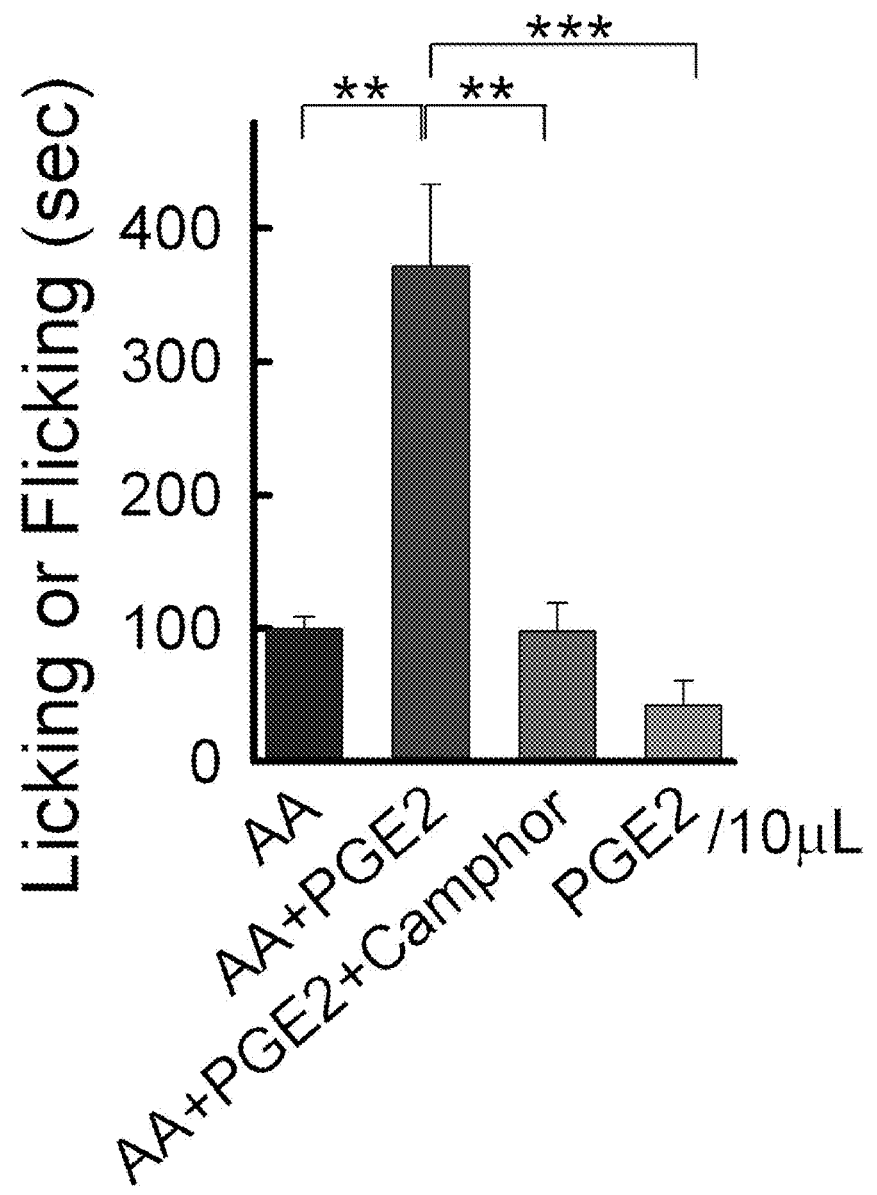

METHOD FOR ACTIVATION OF TRANSIENT RECEPTOR POTENTIAL CATION CHANNEL, SUBFAMILY A, MEMBER 1 USING ACETALDEHYDE

TECHNICAL FIELD

The present invention relates to a method for activation of TRPA1 (transient receptor potential cation channel, subfamily A, member 1) using acetaldehyde.

BACKGROUND ART

TRPA1 (Transient Receptor Potential Cation Channel, Subfamily A, member 1) was first found in peripheral sensory nerve fibers in 2003 owing to the studies in the fields of human physiology and pharmacology. TRPA1 is activated by detecting diverse stimuli including cold temperature, inflammatory and mechanical stresses, etc. And human body feels pain by the activation. TRPA1 belongs to thermoTRP family (temperature-sensitive transient receptor potential ion channels) that is the pain receptor family recognizing temperature and painful stimuli. Many researchers expect that human pain mechanism will be disclosed by understanding the functions of TRPA1, the pain receptor, and finally the goal of relieving pain will be achieved by the development of a TRPA1 regulator.

Studies have been actively undergoing to relieve pain, but the mechanism of hangover pain caused by heavy ethanol intake or drinking has not been explained, yet. It is most likely that hangover pain is induced by acetaldehyde and prostaglandin. The conventional hangover pain relievers developed so far are all to reduce the in vivo concentration of acetaldehyde or prostaglandin, the hangover pain inducer, though whose mechanisms are unknown. A screening method of a hangover pain reliever in relation to the activation of TRPA1 has not been established, yet.

To understand basic techniques used for the development of a hangover pain reliever based on the inhibition of TRPA1 activation, it is important to understand the characteristics of TRPA1. TRPA1 is an ion channel and its activation makes cations to migrate into sensory neurons, causing the changes in membrane currents. The changes of membrane currents generate action potential signal and this potential signal is transmitted to the brain where pain is recognized. One of the techniques to measure the TRPA1 activation is patch-clamp electrophysiology technique measuring the changes of membrane currents after amplifying thereof. And another technique to measure the TRPA1 activation is to measure intracellular calcium level based on the fact that TRPA1 is involved in the migration of cations such as calcium ions. The first technique is superior in sensitivity to the second one, but the second technique is superior in high speed to the first one, so that they are complementary to each other. Such techniques to measure the TRPA1 activation can be executed by the support of animal neuron culture technique, cell line culture technique, TRPA1 DNA control and transfection techniques. To screen a TRPA1 inhibitor and to measure its inhibition activity, various TRPA1 specific inhibitor candidates and standard activators are introduced into TRPA1 over-expressing cells and the inhibition effect on the TRPA1 activation thereby was observed.

Therefore, the present inventors constructed transformants expressing TRP and treated them with acetaldehyde, the hangover pain inducer, and other chemicals known as TRP inhibitors, followed by comparison of the results. As a result, the inventors completed this invention by confirming that acetaldehyde activated TRPA1 specifically and thus it can be effectively used for the screening of a hangover pain reliever.

DISCLOSURE

Technical Problem

It is an object of the present invention to provide a method for screening a TRPA1 activation inhibitor using acetaldehyde, the activator having TRPA1-specific activity.

Technical Solution

To achieve the above object, the present invention provides a method for activation of TRPA1 (transient receptor potential cation channel, subfamily A, member 1) in vitro comprising the step of treating acetaldehyde to isolated neurons.

The present invention also provides a method for isolating TRPA1 positive neurons comprising the following steps:
1) culturing the neurons isolated from a subject and treating them with acetaldehyde;
2) measuring calcium ion channel activity of the neurons treated in step 1); and,
3) comparing the TRPA1 activity measured in step 2) with the TRAP1 activity of neurons not-treated with acetaldehyde; and
4) identifying neurons activated by acetaldehyde as TRPA1 positive neurons.

The present invention also provides a method for isolating TRPA1 negative neurons comprising the following steps:
1) culturing neurons isolated from a subject and treating them with acetaldehyde and a non-specific TRPA1 activator stepwise in that order or in reverse order;
2) measuring the activity of calcium ion channel in the neurons treated in step 1);
3) comparing the calcium channel activity measured in step 2) with that of the neurons not treated with acetaldehyde and the non-specific TRPA1 activator; and
4) identifying neurons activated by the non-specific TRPA1 activator but not activated by acetaldehyde as TRPA1 negative neurons.

The present invention also provides a method for screening a TRPA1 activation blocker comprising the following steps:
1) treating TRPA1 positive neurons with acetaldehyde and TRPA1 activation blocker candidates;
2) treating TRPA1 negative neurons with the above TRPA1 activation blocker candidates and a non-specific TRPA1 activator;
3) measuring the calcium ion channel activities of both TRPA1 positive neurons treated in step 1) and TRPA1 negative neurons treated in step 2);
4) comparing the activity of each calcium ion channel of step 3) with that of TRPA1 positive neurons treated with acetaldehyde alone; and
5) identifying candidates which inhibit the calcium ion channel activity of TRPA1 positive neurons treated with acetaldehyde and TRPA1 activation blocker candidates but do not affect the calcium ion channel activity of TRPA1 negative neurons treated with the TRPA1 activity candidates and the non-specific TRPA1 activator as TRPA1 activation blockers.

The present invention also provides a method for screening a TRPA1 activation blocker comprising the following steps:
1) constructing a transformant by transfecting a host cell with a plasmid containing polynucleotide encoding TRPA1;
2) treating the transformant with acetaldehyde and TRPA1 activation blocker candidates;

3) treating TRPA1 negative neurons with the TRPA1 activation blocker candidates and a non-specific TRPA1 activator;

4) measuring the TRPA1 calcium ion channel activities of both the transformant of step 2) and TRPA1 negative neurons of step 3);, 5) comparing each activity measured in step 4) with the activity of the transformant treated with acetaldehyde alone; and 6) identifying candidates which inhibit the calcium ion channel activity of the transformant treated with acetaldehyde and hangover pain reliever candidates but do not affect the calcium ion channel activity of TRPA1 negative neurons treated with the hangover pain reliever candidates and the non-specific TRPA1 activator as hangover pain relievers.

The present invention also provides a method for screening a TRPA1 activity regulator comprising the following steps:

1) treating a subject with acetaldehyde and TRPA1 activation blocker candidates;

2) measuring nociceptive behaviors induced in the subject treated in step 1);

3) comparing the nociceptive behaviors measured in step 2) with those of the subject treated with acetaldehyde alone; and 4) identifying candidates inducing nociceptive behaviors as TRPA1 activity regulators.

The present invention also provides a method for screening a hangover pain reliever comprising the following steps:

1) treating TRPA1 positive neurons with acetaldehyde and hangover pain reliever candidates;

2) treating TRPA1 negative neurons with the hangover pain reliever candidates and a non-specific TRPA1 activator;

3) measuring the calcium ion channel activities of both TRPA1 positive neurons treated in step 1) and TRPA1 negative neurons treated in step 2);, 4) comparing each activity measured in step 3) with the activity of TRPA1 positive neurons treated with acetaldehyde alone; and 5) identifying candidates which inhibit the calcium ion channel activity of TRPA1 positive neurons treated with acetaldehyde and hangover pain reliever candidates but do not affect the calcium ion channel activity of TRPA1 negative neurons treated with the hangover pain reliever candidates and the non-specific TRPA1 activator as hangover pain relievers.

In addition, the present invention provides a method for screening of a hangover pain reliever comprising the following steps:

1) constructing a transformant prepared by transfecting a host cell with a plasmid containing polynucleotide encoding TRPA1;

2) treating the transformant with acetaldehyde and hangover pain reliever candidates;

3) treating TRPA1 negative neurons with the hangover pain reliever candidates and a non-specific TRPA1 activator;

4) measuring the TRPA1 calcium ion channel activities of both the transformant of step 2) and TRPA1 negative neurons of step 3);, 5) comparing each activity measured in step 4) with the activity of the transformant treated with acetaldehyde alone; and 6) identifying candidates which inhibit the calcium ion channel activity of the transformant treated with acetaldehyde and hangover pain reliever candidates but do not affect the calcium ion channel activity of TRPA1 negative neurons treated with the hangover pain reliever candidates and the non-specific TRPA1 activator as hangover pain relievers.

Advantageous Effect

Acetaldehyde of the present invention works on TRPA1 specifically so that it facilitates the isolation of sensory neurons expressing TRPA1. Therefore, acetaldehyde of the invention can be effectively used for the studies on TRPA1 mechanisms and the development of a TRPA1 based anodyne.

DESCRIPTION OF DRAWINGS

The application of the preferred embodiments of the present invention is best understood with reference to the accompanying drawings, wherein:

FIG. 1 is a set of graphs illustrating the TRPA1 activation by acetaldehyde (AA: acetaldehyde, CA: cinnamaldehyde, RR: a non-specific TRP ion channel blocker, ruthenium red, Camphor: a TRPA1-specific blocker, camphor; means ±S.E.M.):

a: Elevation of intracellular calcium levels in hTRPA1-transfected HEK293T cells (n=17) by the treatment of 1 mM acetaldehyde, 300 µM cinnamaldehyde and 300 µM ATP shown in Fluo-3 calcium imaging;

b: Current-voltage relation of TRPA1 responding by the treatment of 1 mM acetaldehyde, 1 mM acetaldehyde+2 mM camphor and 300 µM cinnamaldehyde (n=5):

Inset: Current-voltage curves measured in three places (A, B and C);

c-d: Suppression of TRPA1 activation to acetaldehyde by TRPA1 blockers (1 mM acetaldehyde+2 mM camphor, 1 mM acetaldehyde+10 µM ruthenium red, 1 mM acetaldehyde):

c: hTRPA1-expressing cells (n=12); and, d: mTRPA1-expressing cells (n=21).

FIG. 2 is a set of graphs illustrating the TRPA1-specific activity of acetaldehyde (AA: acetaldehyde, CA: cinnamaldehyde, RR: a non-specific TRP ion channel blocker, ruthenium red, Camphor: a TRPA1-specific blocker, camphor, EtOH: ethanol, MeOH: methanol, ND: not detected, GdCl3: a TRPA1 blocker, gadolinium, V1: TRPV1, V2: TRPV2, V3: TRPV3, V4: TRPV4, A1: TRPA1, M8: TRPM8; means ±S.E.M.):

a: Dose-response curves for acetaldehyde on hTRPA1 (Kd: 76.5 µM and n: 2.4) and mTRPA1 (Kd: 1.19 mM and n: 3.1) in Fluo-3 calcium imaging (Open circle: hTRPA1-expressing cells, n=22-53; Closed circle: mTRPA1-expressing cells, n=50-120);

b: Calcium levels in hTRPA1-expressing cells (n=12) treated with 10 mM acetic acid, 1% methanol, 1% ethanol, 1 mM acetaldehyde, 300 µM cinnamaldehyde and 300 µM ATP;

c: Responses to acetaldehyde of cells transfected with other sensory TRP channels (***$p<0.001$ and ND: $p>0.05$); and, d: Acetaldehyde (1 mM) evoked outward rectifying current increase in cultured trigeminal neurons (n=6). The current was inhibited by co-application of TRPA1 blockers, GdCl3 (20 µM) and camphor (2 mM):

Inset: Current-voltage curves measured in three places (A, B and C).

FIG. 3 is a set of graphs illustrating that acetaldehyde responses in TRPA1-positive neurons are potentiated by prostaglandin E2 (PGE2) (AA: acetaldehyde, CA: cinnamaldehyde, CAP: capsaicin, BIM: bisindolmaleimide):

a: Acetaldehyde response of neurons in Fluo-3 calcium imaging;

1: Menthol-positive neurons (n=36) did not show acetaldehyde response;

2: Capsaicin positive-cinnamaldehyde-negative neurons (n=102) did not show acetaldehyde response; and, 3: Capsaicin-cinnamaldehyde-positive neurons (n=19) showed acetaldehyde response;

b: The response to 1 mM acetaldehyde during incubation of 1 μM PGE2 was greater than to 1 mM acetaldehyde alone in capsaicin/cinnamaldehyde-positive neurons (n=8) (110.7±3.7% increase, P<0.005);

c: Dose-response curves for acetaldehyde alone (Kd: 740.2 μM, n: 1.8) and 1 mM acetaldehyde+2 min incubation of 1 μM PGE2 (Kd: 90.6 μM, n: 2.1) in Fluo-3 calcium imaging of cultured mouse trigeminal neurons:

(Closed circle: 1 mM acetaldehyde alone, n=12-26; Open circle: 1 mM acetaldehyde+2 min incubation of 1 μM PEG2, n=6-45); and, d: Effect of intracellular signaling modulators on potentiated acetaldehyde responses under PGE2 incubation: SC-51089 (10 μM, n=6), U73122 (3 μM, n=5), bisindolmaleimide (BIM, 1 μM, n=7) and chelerythrine (1 μM, n=11)->suppressed the PGE2-induced potentiation;

U73343 (3 μM, n=5), H-89 (10 μM, n=14)->not suppressed the PGE2-induced potentiation; and, Forskolin (10 μM, n=20)->failed to mimic the PGE2-induced potentiation:

(. * p<0.001,  p<0.01, * p<0.05).

FIG. 4 is a set of graphs illustrating that acetaldehyde induces acute nociceptive behaviors in mice (AA: acetaldehyde, CA: cinnamaldehyde, RR: a non-specific TRP ion channel blocker, ruthenium red, Camphor: a TRPA1-specific blocker, camphor, PGE2: prostaglandin E2, GdCl3: a TRPA1 blocker, gadolinium) (*P<0.001, P<0.01, *P<0.05):

a: Licking/flicking behaviors in mice treated with acetaldehyde (100 mM in 10 μl, n=5), cinnamaldehyde (10 mM in 10 μl, n=5) or vehicle (control, 10 μl PBS, n=5) administered intradermally into hindpaws for the 10-min period immediately following the injection;

b: Sums of the time spent in licking/flicking behaviors for 10 min immediately after drug injection [control (10 μl PBS), 10 mM camphor, 10 mM CA, 10 mM CA+10 mM camphor, 10 mM CA+100 μM GdCl3, 10 mM CA+1 mM GdCl3, 100 mM AA, 100 mM AA+10 mM camphor, 100 mM AA+1 mM RR, 100 mM AA+100 μM GdCl3 or 100 mM AA+1 mM GdCl3];

c: Time spent in licking/flicking behaviors increased along with increasing dose of intradermal acetaldehyde;

d: Licking/flicking behaviors in mice treated with 100 mM AA, 100 mM AA+1 μM PGE2 or 100 mM AA+1 μM PGE2+ 10 mM camphor (10 μl) administered intradermally into hindpaws for the 10-min period immediately following the injection; and e: Sums of the time spent in licking/flicking behaviors for 10 min immediately after drug injection [100 mM AA, 100 mM AA+1 μM PGE2, 100 mM AA+1 μM PGE2+10 mM camphor (10 μl) or 1 μM PGE2 (10 μl)].

BEST MODE

Hereinafter, the present invention is described in detail.

The present invention provides a method for activation of TRPA1 (transient receptor potential cation channel, subfamily A, member 1) in vitro comprising the step of treating acetaldehyde to isolated neurons.

Acetaldehyde stimulates the activation of TRPA1. The acetaldehyde is regarded as a hangover pain inducer. In a preferred embodiment of the present invention, the inventors examined the effect of acetaldehyde, hangover pain inducer, or cinnamaldehyde known as the conventional TRPA1 specific activator on TRPA1. Particularly, these two substances were treated to the transformed cell line expressing TRPA1, and then intracellular calcium levels were investigated by calcium imaging, one of the techniques measuring intracellular calcium level changes. As a result, the above two substances accelerated the activation of TRPA1 (see FIG. 1a). Also, the above two substances were injected to hindpaws of mice, followed by investigation of acute licking or flicking behavior. As a result, time spent in licking/flicking behaviors increased (see FIG. 4a). The acetaldehyde mediated TRPA1 activity was dose-dependent (see FIG. 2a and FIG. 4c) and this activity was suppressed by a TRPA1-specific blocker, camphor, a non-specific TRP ion channel blocker, ruthenium red and another TRPA1 blocker, gadolinium (GdCl3) (see FIGS. 1b-1d, FIG. 2d and FIG. 4b). In the meantime, ethanol acetaldehyde or acetic acid, the intermediate substances of ethanol metabolism, producing and methanol, the simplest form of alcohol, failed to elevate intracellular calcium levels in TRPA1-expressing cells, whereas acetaldehyde of the present invention activated TRPA1 (see FIG. 2b).

Acetaldehyde activates TRPA1 specifically. In a preferred embodiment of the present invention, the TRP channel specificity of acetaldehyde was examined using the transformed cells expressing individual sensory neuronal TRPs, TRPV1, TRPV2 (transient receptor potential vanilloid 2), TRPV3, TRPV4 and TRPM8 (transient receptor potential cation channel, subfamily M, member 8). As a result, only TRPA1 showed a remarkable sensitivity to acetaldehyde in terms of its activation (see FIG. 2c).

In addition, prostaglandin E2 (PGE2) may be additionally treated along with acetaldehyde. The prostaglandin E2 are potent inflammatory mediators and they sensitize nociceptive sensory fibers (Samad et al., 2002; Moriyama et al., 2005), and are supposedly hangover pain inducers. The specific activation of TRPA1 by acetaldehyde is increased by PGE2. In a preferred embodiment of the present invention, the response to acetaldehyde during incubation of PGE2 was greater than to acetaldehyde alone in capsaicin/cinnamaldehyde-positive neurons (see FIGS. 3a and 3b). The activation by the co-treatment with PGE2 was also dose-dependent just like the activation by acetaldehyde (see FIG. 3c). In another preferred embodiment of the present invention, the present inventors further examined which intracellular signaling pathways were involved in the potentiation by PGE2 (see FIG. 3d). An EP1 receptor antagonist SC-51089 significantly blocked the potentiation, suggesting that EP1 receptor-mediated signaling is important in this potentiation. A phospholipase C (PLC) inhibitor U73122, but not an inactive analogue of U73122, was able to suppress the PGE2 effect. Protein kinase C (PKC) inhibitors, bisindolmaleimide (BIM) and chelerythrine also inhibited the PGE2-induced potentiation. On the other hand, a protein kinase A (PKA) inhibitor H-89 caused no change in the potentiation of acetaldehyde responses. Forskolin, which activates adenylyl cyclase leading to PKA activation, also failed to show a PGE2-like potentiating effect, which indicates that PKA is not involved in the potentiation by short-term PGE2 incubation. Overall data suggest that presumptive TRPA1-positive neurons compose acetaldehyde-sensitive neuronal population, and the responses of these neurons are potentiated by PGE2 via PLC and PKC-dependent signaling pathways. Because it is recognized that TRPA1 is an important pain detector (Bautista et al., *Cell* 124:1269-1282, 2006;

Kwan et al., *Neuron* 50:277-289, 2006), these findings may reflect that acetaldehyde elicits pain via the activation of TRPA1-expressing sensory neurons and that PGE2 exacerbates the pain by elevating their acetaldehyde sensitivity. The present inventors next tested whether PGE2 enhanced the behavioral effect of acetaldehyde. The periods during which mice showed the behavioral responses to co-administration of acetaldehyde and PGE2 were dramatically longer compared with those of acetaldehyde alone or PGE2 alone. The treatment with camphor was also effective at negative modification of the acute pain responses, and thus it is evident that TRPA1 plays an important role in sensitization of the acetaldehyde behavioral response by PGE2. The above results suggest that the mechanism underlying acetaldehyde-induced acute pain is TRPA1 activation by acetaldehyde.

Acetaldehyde has TRPA1-specific activity. Therefore, it can be effectively used for the isolation of TRPA1 positive neurons from sensory neurons. It also helps to understand the mechanism of pain recognition by sensory neurons (ex. sensitivity to heat, chemical and mechanical stimuli) and facilitates the identification of diseases (ex. inflammatory pain, neuropathic pain and pain by adverse drug reaction). Acetaldehyde was administered to animals, followed by investigation of pain behaviors to confirm whether or not TRPA1 activation affected real behaviors. Thereby, among many pains, TRPA1-related pain could be distinguished. In addition, it can also be effectively used for the development of TRPA1 blockers. In the case that acetaldehyde is used for the development of a TRPA1 activator, it can be used as the standard material for TRPA1 activator candidates. In the case that acetaldehyde is used for the development of a TRPA1 blocker, it can be used to confirm whether or not the candidate could interrupt the activation of TRPA1 by acetaldehyde. Acetaldehyde and prostaglandin are believed to be hangover pain inducers, so that these materials can be used for the development of a hangover pain reliever.

The present invention also provides a method for isolating TRPA1 positive neurons comprising the following steps:

1) culturing the neurons isolated from a subject and treating them with acetaldehyde;

2) measuring calcium ion channel activity of the neurons treated in step 1); and, 3) selecting TRPA1 positive neurons by comparing the calcium ion channel activity measured in step 2) with the calcium ion channel activity of neurons not-treated with acetaldehyde.

In a preferred embodiment of the present invention, there are trigeminal neurons which are specifically activated by acetaldehyde (see FIG. 3a). This specific reactivity is very useful for the selection of a TRPA1 blocker and activator and further TRPA1 positive neurons can be isolated by using the novel TRPA1 activator, acetaldehyde.

The subject herein is vertebrates and preferably mammals and more preferably such test animals as rats, rabbits, guinea pigs, hamsters, dogs and cats, and most preferably apes such as chimpanzees and gorillas. The preferable concentration of acetaldehyde of step 1) is 10-10000 μM.

In step 1), prostaglandin E2 (PGE2) can be co-treated with acetaldehyde. The TRPA 1 specific activation by acetaldehyde in TRPA1 positive neurons is increased by PGE2 (see FIG. 3).

In addition, the measuring calcium ion channel activity in step 2) can be performed by whole-cell voltage-clamp recording measuring the changes of membrane currents by amplifying thereof or calcium imaging measuring intracellular calcium level changes based on the founding that TRPA1 is able to move cations such as calcium ions, but not always limited thereto.

The present invention also provides a method for isolating TRPA1 negative neurons comprising the following steps:

1) culturing neurons isolated from a subject and treating them with acetaldehyde and a non-specific TRPA1 activator stepwise in that order or in reverse order;

2) measuring the activity of calcium ion channel in the neurons treated in step 1);

3) selecting comparing the calcium channel activity measured in step 2) with that of the neurons not treated with acetaldehyde and the non-specific TRPA1 activator; and 4) identifying neurons activated bt the non-specific TRPA1 activator but not activated by acetaldehyde as TRPA1 negative neurons.

In step 1), prostaglandin E2 (PGE2) can be co-treated with acetaldehyde. The TRPA 1 specific activation by acetaldehyde is increased by PGE2 (See FIG. 3). The TRPA1 non-specific activator in step 1) is preferably one of the activators of thermoTRP group (temperature-sensitive transient receptor potential ion channels) including TRPA1 such as THC (Delta$^9$-tetrahydrocannabinol) or 2-APB (2-Aminoethoxydiphenyl borate), but not always limited thereto. The preferable concentration of acetaldehyde in step 1) is 10-10000 μM.

In addition, the measuring TRPA1 calcium ion channel activity in step 2) can be performed by whole-cell voltage-clamp recording or calcium imaging measuring intracellular calcium level changes, but not always limited thereto.

The present invention also provides a method for screening a TRPA1 activation blocker comprising the following steps:

1) treating TRPA1 positive neurons with acetaldehyde and TRPA1 activation blocker candidates;

2) treating TRPA1 negative neurons with the above TRPA1 activation blocker candidates and a non-specific TRPA1 activator;

3) measuring the calcium ion channel activities of both TRPA1 positive neurons treated in step 1) and TRPA1 negative neurons treated in step 2);

4) comparing the activity of each calcium ion channel of step 3) with that of TRPA1 positive neurons treated with acetaldehyde alone; and 5) identifying candidates which inhibit the calcium ion channel activity of TRPA1 positive neurons treated with acetaldehyde and TRPA1 activation blocker candidates but do not affect the calcium ion channel activity of TRPA1 negative neurons treated with the TRPA1 activity candidates and the non-specific TRPA1 activator as TRPA1 activation blockers.

In step 1), prostaglandin E2 (PGE2) can be co-treated with acetaldehyde. The TRPA 1 specific activation by acetaldehyde is increased by PGE2 (See FIG. 3). The preferable concentration of acetaldehyde in step 1) is 10-10000 μM.

The TRPA1 positive neurons and the TRPA1 negative neurons are characteristically isolated by the method of the present invention. The candidates of step 1) are selected from the group consisting of natural compounds, synthetic compounds, RNA, DNA, polypeptides, enzymes, proteins, ligands, antibodies, antigens, metabolites of bacteria or fungi and bioactive molecules, but not always limited thereto.

The present invention also provides a method for screening a TRPA1 activation blocker comprising the following steps:

1) constructing a transformant by transfecting a host cell with a plasmid containing polynucleotide encoding TRPA1;

2) treating the transformant with acetaldehyde and TRPA1 activation blocker candidates;

3) treating TRPA1 negative neurons with the TRPA1 activation blocker candidates and a non-specific TRPA1 activator;

4) measuring the TRPA1 calcium ion channel activities of both the transformant of step 2) and TRPA1 negative neurons of step 3);

5) comparing each activity measured in step 4) with the TRPA1 activity of the transformant treated with acetaldehyde alone; and 6) identifying candidates which inhibit the calcium ion channel activity of the transformant treated with acetaldehyde and the TRPA1 activation blocker candidates but do not affect the calcium ion channel activity of TRPA1 negative neurons treated with the TRPA1 activation blocker candidates and the non-specific TRPA1 activator as TRPA1 activation blockers.

The host cell herein is preferably the one that is useful for the studies on calcium channel activity and high throughput inhibitor screening, which is exemplified by HEK cell line, CHO cell line, HeLa cell line, and RBL-2H3 cell line, but not always limited thereto.

In step 2), prostaglandin E2 (PGE2) can be co-treated with acetaldehyde. The TRPA 1 specific activation by acetaldehyde is increased by PGE2 (See FIG. 3). In a preferred embodiment of the present invention, among TRPs known to be expressed in sensory neurons, only TRPA1 showed a remarkable sensitivity to acetaldehyde in terms of its activation (see FIG. 2c). The preferable concentration of acetaldehyde is 10-10000 µM. In a preferred embodiment of the present invention, the $EC_{50}$ (effective concentration 50%) of acetaldehyde on hTRPA1 (76.5 µM) was lower than that on mTRPA1 (1.19 mM) (see FIG. 2a). This suggests that acetaldehyde exerted an action on the TRPA1 activity throughout the micromolar ranges. In a preferred embodiment of the present invention, the TRPA1-specific blocker camphor completely suppressed acetaldehyde responses, so did the general TRP channel blocker ruthenium red (see FIGS. 1b-1d).

The present invention also provides a method for screening a TRPA1 activity regulator comprising the following steps:

1) treating a subject with acetaldehyde and TRPA1 activation blocker candidates;

2) measuring nociceptive behaviors induced in the subject treated in step 1);

3) comparing the nociceptive behaviors measured in step 2) with those of the subject treated with acetaldehyde alone; and 4) identifying candidates inducing nociceptive behaviors as TRPA1 activity regulators.

In step 1), prostaglandin E2 (PGE2) can be co-treated with acetaldehyde. The TRPA 1 specific activation by acetaldehyde is increased by PGE2 (See FIG. 3). In a preferred embodiment of the present invention, acetaldehyde induced nociceptive behaviors in mice and the time spent by mice on the acetaldehyde-induced nociceptive behaviors increased in a dose-dependent manner (see FIGS. 4a and 4b). Co-administration of PGE2 greatly enhanced the acetaldehyde-induced responses (see FIGS. 4d and 4e). In another preferred embodiment of the present invention, acetaldehyde-induces nociceptive behaviors were suppressed by the TRPA1-specific blocker camphor, the TRP ion channel blocker ruthenium red and another TRPA1 blocker gadolinium (GdCl3) (see FIG. 4b).

The subject herein is vertebrates and preferably mammals and more preferably such test animals as rats, rabbits, guinea pigs, hamsters, dogs and cats, and most preferably apes such as chimpanzees and gorillas. The preferable concentration of acetaldehyde of step 2) is 10-100 mM. In step 2), the administration is performed by parenteral administration and preferably by intradermal injection, but not always limited thereto. In step 3), the investigation on nociceptive behaviors is preferably performed by analyzing hindpaw licking/flicking behaviors, but not always limited thereto.

The present invention also provides a method for screening a hangover pain reliever comprising the following steps:

1) treating TRPA1 positive neurons with acetaldehyde and hangover pain reliever candidates;

2) treating TRPA1 negative neurons with the hangover pain reliever candidates and a non-specific TRPA1 activator;

3) measuring the calcium ion channel activities of both TRPA1 positive neurons treated in step 1) and TRPA1 negative neurons treated in step 2);, 4) by comparing each activity measured in step 3) with the activity of TRPA1 positive neurons treated with acetaldehyde alone; and 5) identifying candidates which inhibit the calcium ion channel activity of TRPA1 positive neurons treated with acetaldehyde and hangover pain reliever candidates but do not affect the calcium ion channel activity of TRPA1 negative neurons treated with the hangover pain reliever candidates and the non-specific TRPA1 activator as hangover pain relievers.

In addition, the present invention provides a method for screening of a hangover pain reliever comprising the following steps:

1) constructing a transformant prepared by transfecting a host cell with a plasmid containing polynucleotide encoding TRPA1;

2) treating the transformant with acetaldehyde and hangover pain reliever candidates;

3) treating TRPA1 negative neurons with the hangover pain reliever candidates and a non-specific TRPA1 activator;

4) measuring the TRPA1 calcium ion channel activities of both the transformant of step 2) and TRPA1 negative neurons of step 3);, 5) comparing each activity measured in step 4) with the activity of the transformant treated with acetaldehyde alone; and 6) identifying candidates which inhibit the calcium ion channel activity of the transformant treated with acetaldehyde and hangover pain reliever candidates but do not affect the calcium ion channel activity of TRPA1 negative neurons treated with the hangover pain reliever candidates and the non-specific TRPA1 activator as hangover pain relievers.

Mode For Invention

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of Cell Lines Transfected with TRPV

HEK293T cell line (ATCC CRL-11268) was transiently transfected with plasmid DNA containing polynucleotide encoding hTRPA1 (SEQ. ID. NO: 1), rTRPV2 (SEQ. ID. NO: 2), rTRPV1 (SEQ. ID. NO: 3), mTRPV4 (SEQ. ID. NO: 4), mTRPA1 (SEQ. ID. NO: 5), hTRPV3 (SEQ. ID. NO: 6) or mTRPM8 (SEQ. ID. NO: 7).

Particularly, the HEK293T cell line was transiently transfected with individual TRP channel plasmid (pcDNA3.1 containing polynucleotide encoding hTRPA1, rTRPV2, rTRPV1 or mTRPV4; pcDNA5/FRT containing polynucleotide encoding mTRPA1, hTRPV3 or mTRPM8) 3 μg per 35-mm dish and 600 ng/well of pcDNA3 (Invitrogen Corp., USA; containing green fluorescent protein (GFP) cDNA) using Fugene6 (Roche Diagnostics, USA) according to manufacturer's instruction. The transformed cells were cultured in DMEM/F12 containing 10% FBS and 1% penicillin/streptomycin in a $CO_2$ incubator for 24 hours. The cells were replated onto poly-L-lysine-coated glass coverslips, followed by further culture for 10-24 hours.

EXAMPLE 2

Preparation of Trigeminal Neurons

Trigeminal ganglia were dissected out of decapitated adult ICR mice in cold PBS and treated with 1.5 mg/Ml of collagenase/dispase (Roche Diagnostics, USA) at 37□ for 45 min, and then treated with 0.25% trypsin (Invitrogen, USA) for 15 min. The trigeminal neurons prepared thereby were then plated onto poly-L-lysine-coated coverslips in DMEM/F12 containing 10% FBS, 1% penicillin/streptomycin and 5 ng/Ml of 2.5S NGF (Invitrogen, USA), nerve growth factor (Invitrogen), followed by culture in a $CO_2$ incubator for 48-72 hours.

EXAMPLE 3

Statistical Analysis

All the test results were analyzed by using the two-tailed Student's t-test and shown as means ±SEM. *$p<0.001$, $P<0.01$ and *$P<0.05$.

EXAMPLE 4

Investigation of TRPA1 Activation by Acetaldehyde

<4-1> Compounds Treatment
The TRPA1 transfected cell line (n=17) prepared in Example 1 was treated with 1 mM acetaldehyde (AA; Sigma-Aldrich, USA), 300 μM cinnamaldehyde (CA; MP Biomedicals, USA) and 5-100 μM ATP (Sigma-Aldrich, USA), as shown in FIG. 1a, respectively. Stock solutions were made using water or ethanol, and were diluted with test solutions before use.
<4-2> Measurement of Intracellular Calcium Level Changes by Calcium Imaging
Calcium imaging was performed with the cell line of Example <4-1>.
Particularly, the transfected cell line of Example <4-1> was loaded with Fluo-3AM (5 μM; Sigma Aldrich, USA) in the bath solution (140 mM NaCl, 5 mM KCl, 2 mM $CaCl_2$, 1 mM $MgCl_2$, 10 mM HEPES; adjusted to pH 7.4 with NaOH) containing 0.02% pluronic acid (Invitrogen, USA). Calcium imaging was performed with a confocal microscope (LSM5 Pascal, Carl Zeiss, Germany), and time-lapse images (488 nm excitation/514 nm emission) were collected every 3 seconds using Carl Zeiss ratio tool software (Carl Zeiss, Germany). Mean value curve of calcium influx responses was made by Hill plot ($K_d$: 31.9 μM, n: 2.8).
As a result, as shown in FIG. 1a, TRPA1-specific responses of acetaldehyde and cinnamaldehyde were confirmed in TRPA1 expressing cells. At the end of the experiments, ATP (an activator for the endogenous P2Y receptor in HEK293T cells) was added to check the healthiness of the TRPA1-expressing cells.

EXAMPLE 5

Investigation of Suppression of Acetaldehyde-Mediated TRPA1 Activation by TRPA1 a Specific Blocker <5-1> Compounds Treatment 1
The TRPA1 transfected cell line (n=5) prepared by the method of Example 1 was treated with 1 mM AA, 1 mM AA+2 mM camphor (a TRPA1-specific blocker; Sigma-Aldrich, USA) and 300 μM CA, as shown in FIG. 1b, respectively. Stock solutions were made using water or ethanol, and were diluted with test solutions before use.
<5-2> Whole-Cell Voltage-Clamp Experiment
Whole-cell voltage-clamp recording, one of the patch-clamp techniques, was performed with the transfected cell line of Example <5-1> according to the method of Bandel M et al (*Neuron* 41:849-857, 2004).
Particularly, the extracellular solution (140 mM NaCl, 5 mM KCl, 2 mM $CaCl_2$, 1 mM $MgCl_2$, 10 mM HEPES; titrated to pH 7.4 with NaOH) and the pipette solution (140 mM CsCl, 5 mM EGTA, 10 mM HEPES, 2.0 mM MgATP, 0.2 mM NaGTP; titrated to pH 7.2 with CsOH) were used. The potential was holded at −60 mV for 250 ms, voltage-ramp pulsed from −80 mV to +80 mV for 325 seconds and returned to −60 mV for 250 ms, which was repeated without inter-sweep. This experiment was repeated 5 times.
As a result, as shown in FIG. 1b, pronounced outwardly rectifying current occurred during acetaldehyde application in TRPA1 expressing cells that were responsive to cinnamaldehyde. The current was inhibited by application of the TRPA1 blocker, camphor. Inset shows current-voltage curves measured in three places (A, B and C).
<5-3> Compounds Treatment 2
The hTRPA1 transfected cell line (n=12) and the mTRPA1 transfected cell line (n=21) prepared by the method of Example 1 were treated with 1 mM AA+2 mM camphor, 1 mM AA+10 μM ruthenium red (RR; Sigma-Aldrich, USA) and 1 mM AA, respectively. Stock solutions were made using water or ethanol, and were diluted with test solutions before use. Calcium imaging was performed with the transfected cell line treated as the above by the same manner as described in Example <4-2>.
As a result, as shown in FIG. 1c (hTRPA1) and FIG. 1d (mTRPA1), intracellular calcium influx in relation to TRPA1 activation was suppressed by camphor, a TRPA1-specific blocker, and ruthenium red, a non-specific TRP ion channel blocker.

EXAMPLE 6

Investigation of Acetaldehyde Dose-Dependent TRPA1 Activation

The hTRPA1 transfected cell line (n=22-53) and the mTRPA1 transfected cell line (n=50-120) prepared by the method of Example 1 were treated with acetaldehyde with increasing the concentration from 1 to $10^4$ μM. Calcium imaging was performed with the transfected cell lines treated as the above by the same manner as described in Example <4-2>.
As a result, as shown in FIG. 2a, the EC50 of acetaldehyde on hTRPA1 ($K_d$: 76.5 μM and n: 2.4) was lower than that on mTRPA1 ($K_d$: 1.19 mM and n: 3.1), while acetaldehyde exhibited greater maximum efficacy in mTRPA1 responses. This suggests that acetaldehyde exerted an action on the TRPA1 activity throughout the micromolar and millimolar ranges.

EXAMPLE 7

Investigation of TRPA1 Activation by an Intermediate Substance of Ethanol Metabolism Acetaldehyde is generated during ethanol metabolism in the human body. Thus the present inventors investigated whether other related compounds on the metabolic pathway were also able to activate TRPA1. Ethanol is the precursor of acetaldehyde in the action of alcohol dehydrogenase, and acetic acid is the product of the action of aldehyde dehydrogenase from acetaldehyde. And methanol is the simplest form of alcohol.

Particularly, the hTRPA1 transfected cell line (n=12) prepared by the method of Example 1 was treated with 10 mM acetic acid (Sigma-Aldrich, USA), 1% methanol (Sigma-Aldrich, USA), 1% ethanol (Sigma-Aldrich, USA), 1 mM AA, 300 μM CA and 300 μM ATP, respectively. Calcium imaging was performed with the transfected cell line treated as the above by the same manner as described in Example <4-2>.

As a result, as shown in FIG. 2b, acetic acid, ethanol and methanol failed to elevate intracellular calcium levels in hTRPA1-expressing cells. However, this cell line responded to acetaldehyde or cinnamaldehyde.

EXAMPLE 8

Investigation of Responses to Acetaldehyde in Different TRP Transfected Cell Lines The TRPV1, TRPV2, TRPV3, TRPV4, TRPA1 and TRPM8 transfected cell lines prepared by the method of Example 1 and the non-transfected HEK cell line (control group) were treated with 1 mM acetaldehyde. Calcium imaging was performed with the transfected cell lines treated as the above by the same manner as described in Example <4-2>.

As a result, as shown in FIG. 2c, among 6 TRPs known to be expressed in trigeminal neurons, only TRPA1 was activated by acetaldehyde.

EXAMPLE 9

Investigation of Acetaldehyde Responses in Trigeminal Neurons

The trigeminal neurons prepared by the same manner as described in Example 2 were delayed-treated with 1 mM acetaldehyde, followed by treatment of 20 μM GdCl3 (a TRPA1 blocker gadolinium; Sigma-Aldrich, USA) and 2 mM camphor. Then, whole-cell voltage-clamp recording was performed by the same manner as described in Example <5-2>.

As a result, as shown in FIG. 2d, the increased current in trigeminal neurons by the treatment of 1 mM acetaldehyde was inhibited by co-application of TRPA1 blockers, GdCl3 and camphor. Inset shows current-voltage curves measured in three places (A, B and C).

EXAMPLE 10

Investigation of Acetaldehyde Responses in TRPA1 Positive Neurons

The trigeminal neurons prepared by the same manner as described in Example 2 were delayed-treated with 1 mM acetaldehyde, 300 μM menthol (Sigma-Aldrich, USA), 300 μM CA and 2 μM capsaicin (CAP; Sigma-Aldrich, USA), as shown in FIG. 3a. Then, calcium imaging was performed by the same manner as described in Example <4-2>. Menthol is a TRP ligand for TRPM8 and capsaicin is a ligand for TRPV1.

As a result, as shown in FIG. 3a-1 and FIG. 3a-2, menthol-positive neurons (n=36; considered to express TRPM8) and capsaicin-positive/cinnamaldehyde-negative neurons (n=102; considered to express TRPV1) did not show response upon acetaldehyde application. As shown in FIG. 3a-3, capsaicin-cinnamaldehyde-positive neurons (n=19) did response to aldehyde.

EXAMPLE 11

Investigation of Potentiation of Acetaldehyde Responses in TRPA1 Positive Neurons by Prostaglandin E2 (PGE2)

<11-1> Compounds Treatment 1

The capsaicin-cinnamaldehyde-positive neurons (n=8) confirmed in Example 10 were treated with 1 mM AA and 1 μM PGE2 (Sigma-Aldrich, USA)+1 mM AA. Then, calcium imaging was performed by the same manner as described in Example <4-2>. Prostaglandins are potent inflammatory mediators and they potentiate response of nociceptive sensory fibers (Samad et al., 2002; Moriyama et al., 2005).

As a result, as shown in FIG. 3b, sensitivity to acetaldehyde was increased approximately 110.7±3.7% when acetaldehyde was co-treated with prostaglandin, compared with when acetaldehyde was treated alone (P<0.005).

<11-2> Compounds Treatment 2

The trigeminal neurons prepared by the same manner as described in Example 2 were treated with 1 mM AA and 1 μM PGE2 (Sigma-Aldrich, USA)+1 mM AA with increasing the concentration from 0.1 to $10^4$ μM. Then, calcium imaging was performed by the same manner as described in Example <4-2>.

As a result, as shown in FIG. 3c, the $EC_{50}$ of acetaldehyde on the group treated with acetaldehyde alone was higher ($K_d$: 740.2 μM, n: 1.8) than that on the group treated with 1 mM acetaldehyde+1 μM PGE2 ($K_d$: 90.6 μM, n: 2.1). And the maximum efficacy was also heightened by 1.2-fold in the group treated with 1 mM acetaldehyde+1 μM PGE2.

<11-3> Effect of Intracellular Signaling Modulators on Acetaldehyde Responses Potentiated by PGE2

The trigeminal neurons prepared by the same manner as described in Example 2 were treated with 1 μM acetaldehyde, 1 μM PGE2, 1 μM PGE2+10 μM SC-51089 (n=6; Biomol, USA), 1 μM PGE2+3 μM U73122 (n=5; Calbiochem, Germany), 1 μM PGE2+3 μM U73343 (n=5; Calbiochem, Germany), 1 μM PGE2+1 μM BIM (bisindolmaleimide; n=7; Calbiochem, Germany), 1 μM PGE2+1 μM chelerythrine (n=11; Calbiochem, Germany), 1 μM PGE2+ 10 μM H-89 (n=14; Calbiochem, Germany) and 10 μM Forskolin (n=20; Sigma-Aldrich, USA), respectively. Then, calcium imaging was performed by the same manner as described in Example <4-2>.

As a result, as shown in FIG. 3d, the treatment of PGE2+ SC-51089, PGE2+U73122, PGE2+BIM and PGE2+chelerythrine significantly suppressed the PGE2-induced potentiation, while the treatment of PGE2+U73343 and PGE2+H-89 did not suppress the PGE2-induced potentiation. Forskolin failed to mimic the PGE2-induced potentiation.

EXAMPLE 12

Behavioral Analysis on Acute Hindpaw Licking/Flicking

<12-1> Method of Acute Hindpaw Licking/Flicking Behavioral Analysis

This analysis was performed in accordance with protocols approved by the University Committee on Laboratory Animals. Mice were acclimated for 1 h to the test environment prior to experiments. Drugs dissolved in vehicle (PBS containing 0.5% Tween 80) were injected into mice right hindpaws intradermally. The time consumed for the hindpaw licking/flicking behavior in ICR mice (6 weeks) were measured according to the method of Bandell M et al (*Neuron* 41:849-857, 2004) and Moqrich A et al (*Science* 307:1468-1472, 2005), for 10 minutes.

<12-2> Responses to Acetaldehyde in Mice

The mice treated by the method of Example <12-1> were injected with vehicle (10 μl PBS, n=5), 10 mM CA (10 μl, n=5) or 100 mM AA into hindpaws intradermally, followed by observation of licking/flicking behaviors for 10 minutes.

As a result, as shown in FIG. 4a, acetaldehyde elicited acute licking or flicking behavior in mice.

<12-3> Suppression of Acetaldehyde-Induced Responses in Mice

The mice treated by the method of Example <12-1> were injected with vehicle (10 μl PBS, n=5), 10 mM camphor, 10 mM CA (10 μl, n=5), 10 mM CA+10 mM camphor, 10 mM CA+100 μM GdCl3, 10 mM CA+1 mM GdCl3, 100 mM AA (10 μl, n=5), 100 mM AA+10 mM camphor, 100 mM AA+1 mM RR, 100 mM AA+100 μM GdCl3 or 100 mM AA+1 mM GdCl3 into hindpaws intradermally, followed by observation of licking/flicking behaviors for 10 minutes. The blockers including camphor, GdCl3 or RR were injected 5 min prior to the acetaldehyde injection.

As a result, as shown in FIG. 4b, treatment of the TRPA1 blocker, camphor or gadolinium, or the non-specific TRP blocker ruthenium red suppressed acetaldehyde- and cinnamaldehyde-evoked behaviors. In particular, gadolinium, even at a micromolar dose, was able to significantly suppress the nociceptive behaviors when intradermally treated. Treatment of a millimolar level of ruthenium red, a nonspecific TRP blocker, also inhibited the licking/flicking behavior of mice after acetaldehyde.

<12-4> TRPA1 Activation by Acetaldehyde in a Dose-Dependent Manner in Mice

The mice treated by the method of Example <12-1> were injected with vehicle (10 μl PBS, n=5), 1 mM AA, 10 mM AA or 100 mM AA into hindpaws intradermally, followed by observation of licking/flicking behaviors for 10 minutes.

As a result, as shown in FIG. 4c, the acetaldehyde-induced nociceptive behaviors in mice increased in a dose-dependent manner.

<12-5> Responses to PGE2 in Mice

The mice treated by the method of Example <12-1> were injected with 100 mM AA, 1 μM PGE2, 100 mM AA+1 μM PGE2 or 100 mM AA+1 μM PGE2+10 mM camphor (10 μl) into hindpaws intradermally, followed by observation of licking/flicking behaviors for 10 minutes.

As a result, as shown in FIGS. 4d and 4e, the periods during which mice showed the behavioral responses to co-administration of acetaldehyde and PGE2 were dramatically longer compared with those of acetaldehyde alone or PGE2 alone. Intradermal treatment of camphor suppressed the effect of co-injection of acetaldehyde and PGE2. The suppressive effect of camphor on PGE2-potentiated sensitization lasted for 8 min, and it seems that camphor might rapidly diffuse around the injected areas.

The above results indicate that TRPA1 plays an important role in recognizing acetaldehyde-induced behavior potentiated by PGE2. In addition, considering that the PGE2 treatment induced moderate acute pain behaviors, PGE2 is believed to potentiate acetaldehyde-induced behaviors. The results suggest that the mechanism underlying acetaldehyde-induced acute pain is TRPA1 activation by acetaldehyde.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for activation of isolated TRPA1 (transient receptor potential cation channel, subfamily A, member 1) neurons in vitro, said method comprising the step of treating isolated TRPA1 neurons with acetaldehyde and further treating said isolated TRPA1 neurons with prostaglandin E2.

2. A method for identifying TRPA1 (transient receptor potential cation channel, subfamily A, member 1) positive neurons, said method comprising the steps of:
   1) culturing neurons isolated from a subject and treating them with acetaldehyde;
   2) measuring calcium ion channel activity of the neurons treated in step 1);
   3) comparing the calcium ion channel activity measured in step 2) with calcium ion channel activity of neurons not treated with acetaldehyde; and
   4) identifying neurons in which calcium ion channel activity is increased after treating with acetaldehyde as TRPA1 positive neurons.

3. The method according to claim 2, wherein the isolated TRPA1 neurons are further treated with prostaglandin E2 in step 1).

4. The method for according to claim 2, wherein the isolated TRPA1 neurons are treated with acetaldehyde at a concentration of 10 to 10,000 μM in step 1).

5. The method according to claim 2, wherein the step of measuring calcium ion channel activity in step 2) is performed by a whole-cell voltage-clamp technique or calcium imaging.

6. A method for identifying TRPA1 (transient receptor potential cation channel, subfamily A, member 1) negative neurons, said method comprising the steps of:
   1) culturing neurons isolated from a subject and treating them with acetaldehyde and a non-specific TRPA1 activator stepwise in that order or in reverse order to produce treated neurons;
   2) measuring calcium ion channel activity in the treated neurons of step 1);
   3) comparing the calcium channel activity measured in step 2) with that of the neurons not treated with acetaldehyde and the non-specific TRPA1 activator; and
   4) identifying neurons activated by the non-specific TRPA1 activator, but not activated by acetaldehyde, as TRPA1 negative neurons.

7. The method according to claim 6, wherein the isolated neurons are further treated with prostaglandin E2 in step 1).

8. The method according to claim 6, wherein the acetaldehyde in step 1) is at a concentration of 10 to 10,000 μM.

9. The method according to claim 6, wherein the non-specific TRPA1 activator of step 1) is THC (delta9-tetrahydrocannabinol) or 2-APB (2-aminoethoxydiphenyl borate).

10. The method according to claim 6, wherein the measuring calcium ion channel activity in step 2) is performed by a whole-cell voltage-clamp technique or calcium imaging.

* * * * *

SEQUENCE LISTING

```
<160> NUMBER OF SEQ ID NOS: 7

<210> SEQ ID NO 1
<211> LENGTH: 3360
<212> TYPE: DNA
<213> ORGANISM: Artificial Sequence
<220> FEATURE:
<223> OTHER INFORMATION: Synthetic construct:  hTRPA1

<400> SEQUENCE: 1
atgaagcgca gcctgaggaa gatgtggcgc cctggagaaa agaaggagcc ccagggcgtt      60
gtctatgagg atgtgccgga cgacacggag gatttcaagg aatcgcttaa ggtggttttt     120
gaaggaagtg catatggatt acaaaacttt aataagcaaa agaaattaaa aagatgtgac     180
gatatggaca ccttcttctt gcattatgct gcagcagaag gccaaattga gctaatggag     240
aagatcacca gagattcctc tttggaagtg ctgcatgaaa tggatgatta tggaaatacc     300
```

```
cctctgcatt gtgctgtaga aaaaaaccaa attgaaagcg ttaagtttct tctcagcaga    360
ggagcaaacc caaatctccg aaacttcaac atgatggctc ctctccacat agctgtgcag    420
ggcatgaata atgaggtgat gaaggtcttg cttgagcata aaactattga tgttaatttg    480
gaaggagaaa atggaaacac agctgtgatc attgcgtgca ccacaaataa tagcgaagca    540
ttgcagattt tgcttaaaaa aggagctaag ccatgtaaat caaataaatg gggatgtttc    600
cctattcacc aagctgcatt ttcaggttcc aaagaatgca tggaaataat actaaggttt    660
ggtgaagagc atgggtacag tagacagttg cacattaact ttatgaataa tgggaaagcc    720 accctctcc acctggctgt gcaaaatggt gacttggaaa tgatcaaaat gtgcctggac     780
aatggtgcac aaatagaccc agtggagaag ggaaggtgca cagccattca ttttgctgcc    840
acccagggag ccactgagat tgttaaactg atgatatcgt cctattctgg tagcgtggat    900
attgttaaca caaccgatgg atgtcatgag accatgcttc acagagcttc attgtttgat    960
caccatgagc tagcagacta tttaatttca gtgggagcag atattaataa gatcgattct   1020
gaaggacgct ctccacttat attagcaact gcttctgcat cttggaatat tgtaaatttg   1080
ctactctcta aaggtgccca agtagacata aaagataatt ttggacgtaa ttttctgcat   1140
ttaactgtac agcaaccttta tggattaaaa atctgcgac ctgaatttat gcagatgcaa   1200
cagatcaaag agctggtaat ggatgaagac aacgatgggt gtactcctct acattatgca   1260
tgtagacagg ggggccctgg ttctgtaaat aacctacttg gctttaatgt gtccattcat   1320
tccaaaagca aagataagaa atcacctctg cattttgcag ccagttatgg gcgtatcaat   1380
acctgtcaga ggctcctaca agacataagt gatacgaggc ttctgaatga aggtgacctt   1440 catgaatga ctcctctcca tctggcagca aagaatggac atgataaagt agttcagctt    1500
cttctgaaaa aaggtgcatt gtttctcagt gaccacaatg gctggacagc tttgcatcat   1560
gcgtccatgg gcgggtacac tcagaccatg aaggtcattc ttgatactaa tttgaagtgc   1620
acagatcgcc tggatgaaga cgggaacact gcacttcact ttgctgcaag ggaaggccac   1680
gccaaagccg ttgcgcttct tctgagccac aatgctgaca tagtcctgaa caagcagcag   1740
gcctcctttt tgcaccttgc acttcacaat aagaggaagg aggttgttct tacgatcatc   1800
aggagcaaaa gatgggatga atgtcttaag attttcagtc ataattctcc aggcaataaa   1860
tgtccaatta cagaaatgat agaataccctc cctgaatgca tgaaggtact tttagatttc   1920
tgcatgttgc attccacaga agacaagtcc tgccgagact attatatcga gtataatttc   1980
aaatatcttc aatgtccatt agaattcacc aaaaaaacac ctacacagga tgttatatat   2040
gaaccgctta cagccctcaa cgcaatggta caaaataacc gcatagagct tctcaatcat   2100
cctgtgtgta aagaatattt actcatgaaa tggttggctt atggatttag agctcatatg   2160
atgaatttag gatcttactg tcttggtctc ataccctatga ccattctcgt tgtcaatata   2220
aaaccaggaa tggctttcaa ctcaactggc atcatcaatg aaactagtga tcattcagaa   2280
atactagata ccacgaattc atatctaata aaaaacttgta tgattttagt gttttatca   2340 agtatatttg ggtattgcaa agaagcgggg caaattttcc aacagaaaag gaattatttt   2400
atggatataa gcaatgttct tgaatggatt atctacacga cgggcatcat ttttgtgctg   2460
cccttgtttg ttgaaatacc agctcatctg cagtggcaat gtggagcaat tgctgtttac   2520
ttctattgga tgaatttctt attgtatctt caaagatttg aaaattgtgg aattttatt   2580 gttatgttgg aggtaatttt gaaaactttg ttgaggtcta cagttgtatt tatcttcctt   2640
cttctggctt ttggactcag cttttacatc ctcctgaatt tacaggatcc cttcagctct   2700
```

-continued

| | |
|---|---|
| ccattgcttt ctataatcca gaccttcagc atgatgctag agatatcaa ttatcgagag | 2760 |
| tccttcctag aaccatatct gagaaatgaa ttggcacatc cagttctgtc ctttgcacaa | 2820 |
| cttgtttcct tcacaatatt tgtcccaatt gtcctcatga atttacttat tggtttggca | 2880 |
| gttggcgaca ttgctgaggt ccagaaacat gcatcattga agaggatagc tatgcaggtg | 2940 |
| gaacttcata ccagcttaga gaagaagctg ccactttggt ttctacgcaa agtggatcag | 3000 |
| aaatccacca tcgtgtatcc caacaaaccc agatctggtg ggatgttatt ccatatattc | 3060 |
| tgtttttat tttgcactgg ggaaataaga caagaaatac caaatgctga taaatctta | 3120 |
| gaaatggaaa tattaaagca gaaataccgg ctgaaggatc ttacttttct cctggaaaaa | 3180 |
| cagcatgagc tcattaaact gatcattcag aagatggaga tcatctctga gacagaggat | 3240 |
| gatgatagcc attgttcttt tcaagacagg tttaagaaag agcagatgga acaaaggaat | 3300 |
| agcagatgga atactgtgtt gagagcagtc aaggcaaaaa cacaccatct tgagccttag | 3360 |

<210> SEQ ID NO 2
<211> LENGTH: 2768
<212> TYPE: DNA
<213> ORGANISM: Artificial Sequence
<220> FEATURE:
<223> OTHER INFORMATION: Synthetic construct: rTRPV2

<400> SEQUENCE: 2

| | |
|---|---|
| ctgctctgtc cactgtgtga gacgaacagg tggagggtgg acgacgcaga gaaagctcgg | 60 |
| agcgggccgc ggaggttccc acagccccat tactgtcagc gttgagccgc accccctccgg | 120 |
| gccgcacttc ctctctcagt ccccgctgcc ggagagcccc gctaggctcg gtgatcctag | 180 |
| cctgcagttt gccgccgcta caccttggct tcagcctgcg ggcccctctc catcaccttc | 240 |
| tccaggtccc agccaggcct gccctgcgg tatgagagag gaaccttaac atctccatct | 300 |
| ctacagaggt ttcagctgta aggagcatcc tcctctctca ggatgacttc agcctccagc | 360 |
| cccccagctt tcaggctgga gacttccgat ggagatgaag agggcaatgc tgaggtgaac | 420 |
| aaggggaagc aggaaccgcc cccatggag tcaccattcc agagggagga ccggaattcc | 480 |
| tccctcaga tcaaagtgaa cctcaacttc ataaagagac ctcctaaaaa cacttctgct | 540 |
| cccagccagc aggagccaga tcggtttgac cgtgaccgac tcttcagtgt ggtctcccgg | 600 |
| ggtgtccccg aggaactgac tggactgcta gaataccctgc gctggaacag caagtacctc | 660 |
| actgactctg catacacaga aggctccact ggaaagacgt gcctgatgaa ggctgtgctg | 720 |
| aaccttcagg atgggggtcaa tgcctgcatc atgccgctgc tgcagattga caaggattcc | 780 |
| ggcaatccca gcccctcgt caatgcccag tgcatcgatg agttctacca aggccacagt | 840 |
| gcgctgcaca tcgccataga aagaggagc ctgcagtgcg tgaagctgct ggtagagaat | 900 |
| ggagcggatg ttcacctccg agcctgtggc cgcttcttcc aaaagcacca aggaacttgt | 960 |
| ttctattttg gagagctacc tcttctctg gctgcgtgca ccaagcagtg ggatgtggtg | 1020 |
| acctacctcc tggagaaccc acaccagccg gccagcctgg aggccaccga ctccctgggc | 1080 |
| aacacagtcc tgcatgctct ggtaatgatt gcagataact cgcctgagaa cagtgccctg | 1140 |
| gtgatccaca tgtacgacgg gcttctacaa atgggggcgc gcctctgccc cactgtgcag | 1200 |
| cttgaggaaa tctccaacca ccaaggcctc acaccctga aactagccgc caaggaaggc | 1260 |
| aaaatcgaga ttttcaggca cattctgcag cgggaattct caggaccgta ccagcccctt | 1320 |
| tcccgaaagt ttactgagtg gtgttacggt cctgtgcggg tatcgctgta cgacctgtcc | 1380 |
| tctgtggaca gctgggaaaa gaactcggtg ctggagatca tcgcttttca ttgcaagagc | 1440 |

```
ccgaaccggc accgcatggt ggttttagaa ccactgaaca agcttctgca ggagaaatgg    1500
gatcggctcg tctcaagatt cttcttcaac ttcgcctgct acttggtcta catgttcatc    1560
ttcaccgtcg ttgcctacca ccagccttcc ctggatcagc cagccatccc ctcatcaaaa    1620 gcgactttg gggaatccat gctgctgctg gccacattc tgatcctgct tgggggtatt     1680
tacctcttac tgggccagct gtggtacttt tggcggcggc gcctgttcat ctggatctca    1740
ttcatggaca gctactttga atcctcttt ctccttcagg ctctgctcac agtgctgtcc     1800
caggtgctgc gcttcatgga gactgaatgg tacctacccc tgctagtgtt atccctagtg    1860
ctgggctggc tgaacctgct ttactacaca cggggctttc agcacacagg catctacagt    1920
gtcatgatcc agaaggtcat ccttcgagac ctgctccgtt tcctgctggt ctacctggtc    1980
ttccttttcg gctttgctgt agccctagta agcttgagca gagaggcccg aagtcccaaa    2040
gcccctgaag ataacaactc cacagtgacg aacagccca cggtgggcca ggaggaggag     2100
ccagctccat atcggagcat tctggatgcc tccctagagc tgttcaagtt caccattggt    2160 atggggagc tggctttcca ggaacagctg cgttttcgtg gggtggtcct gctgttgctg     2220
ttggcctacg tccttctcac ctacgtcctg ctgctcaaca tgctcattgc tctcatgagc    2280
gaaactgtca ccacgttgc tgacaacagc tggagcatct ggaagttgca gaaagccatc    2340
tctgtcttgg agatggagaa tggttactgg tggtgccgga ggaagaaaca tcgtgaaggg    2400
aggctgctga aagtcggcac caggggggat ggtacccctg atgagcgctg gtgcttcagg    2460
gtggaggaag taaattgggt tgcttgggag aagactcttc ccaccttatc tgaggatcca    2520
tcagggccag gcatcactgg taataaaaag aacccaacct ctaaaccggg gaagaacagt    2580
gcctcagagg aagaccatct gccccttcag gtcctccagt cccccctgatg cccagatgc    2640 agcagcaggc tggcaggatg gagtagggaa tcttcccagc cacaccagag gctactgagt    2700
tttggtggaa atataaatat ttttttgcat aaccaaaaaa aaaaaaaaaa aaaaaaaaa     2760 aaaaaagg                                                            2768
```

<210> SEQ ID NO 3
<211> LENGTH: 2847
<212> TYPE: DNA
<213> ORGANISM: Artificial Sequence
<220> FEATURE:
<223> OTHER INFORMATION: Synthetic construct: rTRPV1

<400> SEQUENCE: 3

```
cagctccaag gcacttgctc catttggggt gtgcctgcac ctagctggtt gcaaattggg     60
ccacagagga tctggaaagg atggaacaac gggctagctt agactcagag gagtctgagt    120
ccccacccca agagaactcc tgcctggacc ctccagacag agaccctaac tgcaagccac    180
ctccagtcaa gccccacatc ttcactacca ggagtcgtac ccggcttttt gggaaggtg     240 actcggagga ggcctctccc ctggactgcc ttatgagga aggcgggctg gcttcctgcc     300
ctatcatcac tgtcagctct gttctaacta tccagaggcc tggggatgga cctgccagtg    360
tcaggccgtc atcccaggac tccgtctccg ctggtgagaa gccccgagg ctctatgatc     420 gcaggagcat cttcgatgct gtggctcaga gtaactgcca ggagctggag agcctgctgc    480
ccttcctgca gaggagcaag aagcgcctga ctgcagcga gttcaaagac ccagagacag    540
gaaagacctg tctgctaaaa gccatgctca atctgcacaa tgggcagaat gacaccatcg    600
ctctgctcct ggacgttgcc cggaagacag acagcctgaa gcagtttgtc aatgccagct    660
acacagacag ctactacaag ggccagacag cactgcacat tgccattgaa cggcggaaca    720
```

```
tgacgctggt gaccctcttg gtggagaatg gagcagatgt ccaggctgcg gctaacgggg    780
acttcttcaa gaaaaccaaa gggaggcctg gcttctactt tggtgagctg ccctgtccc     840 tggctgcgtg caccaaccag ctggccattg tgaagttcct gctgcagaac tcctggcagc    900
ctgcagacat cagcgcccgg gactcagtgg gcaacacggt gcttcatgcc ctggtggagg    960
tggcagataa cacagttgac aacaccaagt tcgtgacaag catgtacaac gagatcttga    1020 tcctggggc caaactccac cccacgctga agctggaaga gatcaccaac aggaaggggc     1080
tcacgccact ggctctggct gctagcagtg ggaagatcgg ggtcttggcc tacattctcc    1140
agagggagat ccatgaaccc gagtgccgac acctatccag gaagttcacc gaatgggcct    1200
atgggccagt gcactcctcc ctttatgacc tgtcctgcat tgacacctgt gaaaagaact    1260
cggttctgga ggtgatcgct acagcagca gtgagacccc taaccgtcat gacatgcttc      1320
tcgtggaacc cttgaaccga ctcctacagg acaagtggga cagatttgtc aagcgcatct    1380
tctacttcaa cttcttcgtc tactgcttgt atatgatcat cttcaccgcg ctgcctact     1440 atcggcctgt ggaaggcttg ccccctata agctgaaaaa caccgttggg gactatttcc     1500
gagtcaccgg agagatcttg tctgtgtcag gaggagtcta cttcttcttc cgagggattc    1560
aatatttcct gcagaggcga ccatccctca gagtttgtt tgtggacagc tacagtgaga     1620 tactttttctt tgtacagtcg ctgttcatgc tggtgtctgt ggtactgtac ttcagccaac   1680
gcaaggagta tgtggcttcc atggtgttct ccctggccat gggctggacc aacatgctct    1740
actatacccg aggattccag cagatgggca tctatgctgt catgattgag aagatgatcc    1800
tcagagacct gtgccggttt atgttcgtct acctcgtgtt cttgtttgga ttttccacag    1860
ctgtggtgac actgattgag gatgggaaga ataactctct gcctatggag tccacaccac    1920
acaagtgccg ggggtctgcc tgcaagccag gtaactctta caacagcctg tattccacat    1980
gtctggagct gttcaagttc accatcggca tgggcgacct ggagttcact gagaactacg    2040
acttcaaggc tgtcttcatc atcctgttac tggcctatgt gattctcacc tacatccttc    2100
tgctcaacat gctcattgct ctcatgggtg agaccgtcaa caagattgca caagagagca    2160
agaacatctg gaagctgcag agagccatca ccatcctgga tacagagaag agcttcctga    2220
agtgcatgag gaaggccttc cgctctggca agctgctgca ggtggggttc actcctgacg    2280
gcaaggatga ctaccggtgg tgtttcaggg tggacgaggt aaactggact acctggaaca    2340
ccaatgtggg tatcatcaac gaggacccag gcaactgtga gggcgtcaag cgcacctga     2400 gcttctccct gaggtcaggc cgagtttcag ggagaaactg gaagaacttt gccctggttc    2460
cccttctgag gatgcaagc actcgagata gacatgccac ccagcaggaa gaagttcaac     2520
tgaagcatta tacgggatcc cttaagccag aggatgctga ggttttcaag gattccatgg    2580
tcccagggga gaaataatgg acactatgca gggatcaatg cggggtcttt gggtggtctg    2640
cttagggaac cagcagggtt gacgttatct gggtccactc tgtgcctgcc taggcacatt    2700
cctaggactt cggcgggcct gctgtgggaa ctgggaggtg tgtgggaatt gagatgtgta    2760
tccaaccatg atctccaaac atttggcttt caactcttta tggactttat taaacagagt    2820
gaatggcaaa tctctacttg gacacat                                        2847
```

<210> SEQ ID NO 4
<211> LENGTH: 2616
<212> TYPE: DNA
<213> ORGANISM: Artificial Sequence
<220> FEATURE:
<223> OTHER INFORMATION: Synthetic construct: mTRPV4

<400> SEQUENCE: 4

```
atggcagatc ctggtgatgg tccccgtgca gcgcctgggg aggtggctga gcccctgga     60
gatgagagtg gtacctctgg tggggaggcc ttccccctct cttccctggc caatctgttt    120
gaggggagg aaggctcctc ttctcttccc ccggtggatg ctagccgccc tgctggccct     180
ggcgatggac gtccaaacct gcgtatgaag ttccagggcg cttccgcaa ggggttccc      240
aaccccattg acctgttgga gtccaccctg tacgagtcct cagtagtgcc tgggcccaag    300
aaagcgccca tggattcctt gttcgactac ggcacttacc gtcaccccc cagtgacaac     360
aagagatgga ggagaaaggt cgtggagaag cagccacaga gccccaaagc tcctgcaccc    420
cagccacccc ccatcctcaa agtcttcaat cggcccatcc tctttgacat tgtgtcccgg    480
ggctccactg cggacctaga tggactgctc tccttcttgt tgacccacaa gaagcgcctg    540
actgatgagg agttccggga gccgtccacg gggaagacct gcctgcccaa ggcgctgctg    600
aacctaagca acgggcgcaa cgacaccatc ccggtgttgc tggacattgc ggagcgcacc    660
ggcaacatgc gtgaattcat caactcgccc ttcagagaca tctactaccg aggccagaca    720
tccctgcaca ttgccatcga acggcgctgc aagcactacg tggagctgct ggtggcccag    780
ggagccgacg tgcacgccca ggcccgcggc cgcttcttcc agcccaagga tgagggaggc    840
tacttctact tggggagct gcccttgtcc ctggcagcct gcaccaacca gccgcacatc    900
gtcaactacc tgacagagaa ccctcacaag aaagctgaca tgaggcgaca ggactcgagg    960
gggaacacgt gctgcacgc gctggtggcc atcgccgaca cacccgaga gaacaccaag    1020
tttgtcacca agatgtacga cctgctgctt ctcaagtgtt cacgcctctt ccccgacagc   1080
aacctggaga cagttctcaa caatgatggc ctttcgcctc tcatgatggc tgccaagaca   1140
ggcaagatcg gggtctttca gcacatcatc cgacgtgagg tgacagatga ggacacccgg   1200
catctgtctc gcaagttcaa ggactgggcc tatgggcctg tgtattcttc tctctacgac   1260
ctctcctccc tggacacatg cggggaggag gtgtccgtgc tggagatcct ggtgtacaac   1320
agcaagatcg agaaccgcca tgagatgctg gctgtagagc ccattaacga actgttgaga   1380
gacaagtggc gtaagtttgg ggctgtgtcc ttctacatca acgtggtctc ctatctgtgt   1440
gccatggtca tcttcaccct caccgcctac tatcagccac tggagggcac gccaccctac   1500
ccttaccgga ccacagtgga ctacctgagg ctggctggcg aggtcatcac gctcttcaca   1560
ggagtcctgt tcttctttac cagtatcaaa gacttgttca cgaagaaatg ccctggagtg   1620
aattctctct tcgtcgatgg ctccttccag ttactctact tcatctactc tgtgctggtg   1680
gttgtctctg cggcgctcta cctgctggga atcgaggcct acctggctgt gatggtctttt  1740
gccctggtcc tgggctggat gaatgcgctg tacttcacgc gcgggttgaa gctgacgggg   1800
acctacagca tcatgattca gaagatcctc ttcaaagacc tcttccgctt cctgcttgtg   1860
tacctgctct tcatgatcgg ctatgcctca gccctggtca ccctcctgaa tccgtgcacc   1920
aacatgaagg tctgtgacga ggaccagagc aactgcacgg tgcccacgta tcctgcgtgc   1980
cgcgacagcg agaccttcag cgccttcctc ctggacctct tcaagctcac catcggcatg   2040
ggagacctgg agatgctgag cagcgccaag taccccgtgg tcttcatcct cctgctggtc   2100
acctacatca tcctcacctt cgtgctcctg ttgaacatgc ttatcgccct catgggtgag   2160
accgtggggcc agtgtccaa ggagagcaag cacatctgga gttgcagtg gccaccacc     2220
atcctggaca tcgagcgttc cttccctgtg ttcctgagga aggccttccg ctccggagag   2280
atggtgactg tgggcaagag ctcagatggc actccggacc gcaggtggtg cttcagggtg   2340
```

-continued

| | |
|---|---|
| gacgaggtga actggtctca ctggaaccag aacttgggca tcattaacga ggaccctggc | 2400 |
| aagagtgaaa tctaccagta ctatggcttc tcccacaccg tggggcgcct tcgtagggat | 2460 |
| cgttggtcct cggtggtgcc ccgcgtagtg gagctgaaca agaactcaag cgcagatgaa | 2520 |
| gtggtggtac ccctggataa cctagggaac cccaactgtg acggccacca gcagggctac | 2580 |
| gctcccaagt ggaggacgga cgatgcccca ctgtag | 2616 |

<210> SEQ ID NO 5
<211> LENGTH: 4263
<212> TYPE: DNA
<213> ORGANISM: Artificial Sequence
<220> FEATURE:
<223> OTHER INFORMATION: Synthetic construct: mTRPA1

<400> SEQUENCE: 5

| | |
|---|---|
| gcgccagccg gcgtccaggt ggagtcaatg aagcgcggct tgaggaggat tctgctcccg | 60 |
| gaggaaagga aggaggtcca gggcgttgtc tatcgcggcg tcggggaaga catggactgc | 120 |
| tccaaggaat cctttaaggt ggacattgaa ggagatatgt gtagattaga agacttcatc | 180 |
| aagaaccgaa gaaaactaag caaatatgag gatgaaaatc tctgtcctct gcatcacgca | 240 |
| gcagcagaag gtcaagttga actgatggaa ctgatcatca atggttcttc gtgtgaagtg | 300 |
| ctgaatataa tggatggtta tggaaatacc ccactgcatt gtgctgcaga aaaaaatcaa | 360 |
| gttgaaagtg taaagtttct tctcagccaa ggagcaaatc caaacctccg aaatagaaac | 420 |
| atgatgtcac cccttcacat agctgtgcat ggcatgtaca acgaagtgat caaggtgttg | 480 |
| actgagcaca aggccactaa catcaattta gaaggagaga atgggaacac ggctttgatg | 540 |
| tccacgtgtg ccaaagacaa cagtgaagct ttgcaaattt tgttagaaaa aggagctaag | 600 |
| ctgtgtaaat caaataagtg gggagactac cctgtgcacc aggcagcatt tcaggtgcc | 660 |
| aaaaaatgca tggaattaat cttagcatat ggtgaaaaga acggctacag cagggagact | 720 |
| cacattaatt ttgtgaatca caagaaagcc agccctctcc acctagcagt tcaaagcgga | 780 |
| gacttggaca tgattaagat gtgcctggac aacggtgcac acatcgacat gatggagaat | 840 |
| gccaaatgca tggcccctcca ttttgctgca acccagggag ccactgacat cgttaagctc | 900 |
| atgatctcat cctataccgg aagtagtgat attgtgaatg cagttgatgg caatcaggag | 960 |
| accctgcttc acagagcctc gttatttgat caccatgacc tggcagaata cctaatatca | 1020 |
| gtgggagcag acatcaacag cactgattct gaaggacgct ctccacttat tttagcaaca | 1080 |
| gcttctgcat cctggaacat tgtgaatttg ctcctctgta aaggtccaa agtagacata | 1140 |
| aaagatcatc ttgggcgtaa cttttttgcat ttgactgtgc agcagcctta tggactaaga | 1200 |
| aatttgcggc ctgagtttat gcagatgcaa cacatcaaag agctggtgat ggatgaagac | 1260 |
| aatgacggat gcacacctct ccattatgcc tgtaggcagg gggttcctgt ctctgtaaat | 1320 |
| aacctccttg gcttcaatgt gtccattcat agcaaaagta aagataagaa gtcgcccctg | 1380 |
| cattttgcag ccagttatgg gcgcatcaat acatgtcaga gacttctgca agacataagt | 1440 |
| gatacgaggc ttttgaatga aggggatctc catgggatga cccctctcca cctggcagca | 1500 |
| aaaaatgggc atgataaagt cgttcaactc cttctgaaga aggggccctt atttctcagt | 1560 |
| gaccacaatg gctggactgc tttgcatcac gcctccatgg gtgggtacac tcagaccatg | 1620 |
| aaggtcattc ttgatactaa cttgaaatgc acagaccgac tagatgaaga agggaacaca | 1680 |
| gcactccact ttgcagcacg ggaaggccat gccaaggctt tgcaatgct tttgagctac | 1740 |
| aatgctgaca tcctcctgaa caagaagcaa gcttcctttc tgcatattgc cctgcacaat | 1800 |

```
aagcgcaagg aagtggttct cacaaccatc agaaataaaa gatgggatga gtgtcttcaa    1860
gttttcactc ataattctcc aagcaatcga tgtccaatca tggagatggt agaatacctc    1920
cccgagtgca tgaaagttct tttagatttc tgcatgatac cttccacaga agacaagtcc    1980
tgtcaagact accatattga gtataatttc aagtatctcc aatgcccatt atccatgacc    2040
aaaaaagtag cacctaccca ggatgtggta tatgagcctc ttacaatcct caatgtcatg    2100
gtccaacata accgcataga actcctcaac caccctgtgt gtagggagta cttactcatg    2160
aaatggtgtg cctatggatt cagagcccat atgatgaacc taggatctta ttgtcttggt    2220
ctcatacccc tgacccttct tgttgtcaaa atacagcctg gaatggcctt caattctact    2280
ggaataatca atggaactag tagtactcat gaggaaagaa tagacactct gaattcattt    2340
ccaataaaaa tatgtatgat tctagttttt ttatcaagta tatttggata ttgcaaagaa    2400
gtgatccaaa ttttccaaca gaaaaggaat tacttcctgg attacaacaa tgctctggaa    2460
tgggttatct atacaactag tatcatcttc gtgttgccct tgttcctcaa catcccagcg    2520
tatatgcagt ggcaatgtgg agcaatagcg atattcttct actggatgaa cttcctactg    2580
tatcttcaaa ggtttgagaa ctgtggaatt ttcattgtta tgttggaggt gatttttaaa    2640
acattgctga gatcgaccgg agtgtttatc ttcctcctac tggcttttgg cctcagcttt    2700
tatgttctcc tgaatttcca agatgccttc agcaccccat tgctttcctt aatccagaca    2760
ttcagtatga tgctaggaga catcaattat cgagatgcct tcctagaacc attgtttaga    2820
aatgagttgg catacccagt cctgaccttt gggcagctta ttgccttcac aatgtttgtc    2880
ccaattgttc tcatgaactt actgattggc ttggcggttg gggacattgc tgaggtccag    2940
aagcatgcgt cattgaagag gattgctatg caggtggaac ttcataccaa cttagaaaaa    3000
aagctgccac tctggtactt acgcaaagtg gatcagaggt ccaccatcgt gtatccaaat    3060
agacccaggc acggcaggat gctacggttt tttcattact ttcttaatat gcaagaaaca    3120
cgacaagaag taccaaacat tgacacatgc ttggaaatgg aaatattgaa acagaaatat    3180
cggctgaagg acctcacttc cctcttggaa aagcagcatg agctcatcaa actcatcatc    3240
cagaagatgg agatcatctc agagacagaa gatgaagata accattgctc tttccaagac    3300
aggttcaaga aggagaggct ggaacagatg cacagcaagt ggaattttgt cttaaacgca    3360
gttaagacta aaacacattg ttctattagc cacccggact tttagttctg tgtcttatgg    3420
gagtgggaga ctgctttaca tacttatttc agtgaatttc agtttggaaa agagcaaaga    3480
aacagaaagt tgactaacat tgctgcatgg agatcctagt tcctgcaacc tcacccatac    3540
atatgctcat atttcctgtc aattactatg tattgagaag atcctttctg acatgttcaa    3600
tttgaacatg aaggatagtc tctttcgagt gaataaaaac cagggttgtt ggaatgcata    3660
ttatggagga taagaattaa tgtaactatt aaggcagaac acaactacat aatacaagat    3720
gcatataatt ccaagtatta tatttaatct cctaccatgt taaaccttcc tgtgttataa    3780
cctgtctggg acactataat ctctgttcct actatgatta gatcatagtc tcaccctcct    3840
cgtcccatca cacatgacat cattttgagc cacatgcaga aagtcctagt tagtagactg    3900
tgataagtat gaatgttaca atagaaatgt gttcccttag tgttcatcag ttgtgatggt    3960
ttaaatgaga aacgttgccc acagactcat acatttaaac ccttagtccc agttgttgct    4020
gctgcttagg ggggccacac agccttgctt gctctctcct ttctgagtgt ggagagaaat    4080
gtgatcagta agactcctgc tcctgctgcc atgctcttta ttccattatg gacttcttct    4140
gaaactgcaa gcagaaattc actgttcctt cctcaaattt cttttggtca tggtattata    4200
```

```
tcatagcaac agaaactaac ttatgtacca atggtcttaa taaagaataa agcctgtaca    4260
gtc                                                                 4263

<210> SEQ ID NO 6
<211> LENGTH: 2373
<212> TYPE: DNA
<213> ORGANISM: Artificial Sequence
<220> FEATURE:
<223> OTHER INFORMATION: Synthetic construct: hTRPV3

<400> SEQUENCE: 6
atgaaagccc accccaagga gatggtgcct ctcatgggca agagagttgc tgccccccagt     60 gggaaccctg ccatcctgcc agagaagagg ccggcggaga tcacccccac aaagaagagt    120
gcacacttct tcctggagat agaagggttt gaacccaacc ccacagttgc caagacctct    180
cctcctgtct tctccaagcc catggattcc aacatccggc agtgcatctc tggtaactgt    240
gatgacatgg actcccccca gtctcctcag gatgatgtga cagagacccc atccaatccc    300
aacagcccca gtgcacagct ggccaaggaa gagcagagga ggaaaaagag gcggctgaag    360
aagcgcatct ttgcagccgt gtctgagggc tgcgtggagg agttggtaga gttgctggtg    420
gagctgcagg agctttgcag gcggcgccat gatgaggatg tgcctgactt cctcatgcac    480
aagctgacgg cctccgacac ggggaagacc tgcctgatga aggccttgtt aaacatcaac    540
cccaacacca aggagatagt gcggatcctg cttgcctttg ctgaagagaa cgacatcctg    600
ggcaggttca tcaacgccga gtacacagag gaggcctatg aagggcagac ggcgctgaac    660
atcgccatcg agcggcggca gggggacatc gcagccctgc tcatcgccgc cggcgccgac    720
gtcaacgcgc acgccaaggg ggccttcttc aaccccaagt accaacacga aggcttctac    780
ttcggtgaga cgccctggc cctggcagca tgcaccaacc agcccgagat tgtgcagctg    840
ctgatggagc acgagcagac ggacatcacc tcgcgggact cacgaggcaa caacatcctt    900
cacgccctgg tgaccgtggc cgaggacttc aagacgcaga atgactttgt gaagcgcatg    960
tacgacatga tcctactgcg gagtggcaac tgggagctgg agaccactcg caacaacgat   1020
ggcctcacgc cgctgcagct ggccgccaag atgggcaagg cggagatcct gaagtacatc   1080
ctcagtcgtg agatcaagga gaagcggctc cggagcctgt ccaggaagtt caccgactgg   1140
gcgtacggac ccgtgtcatc ctccctctac gacctcacca acgtggacac caccacggac   1200
aactcagtgc tggaaatcac tgtctacaac accaacatcg acaaccggca tgagatgctg   1260
accctggagc cgctgcacac gctgctgcat atgaagtgga agaagtttgc caagcacatg   1320
ttctttctgt ccttctgctt ttatttcttc tacaacatca ccctgaccct cgtctcgtac   1380
taccgccccc gggaggagga ggccatcccg cacccttgg ccctgacgca aagatgggg   1440 tggctgcagc tcctagggag gatgtttgtg ctcatctggg ccatgtgcat ctctgtgaaa   1500
gagggcattg ccatcttcct gctgagaccc tcggatctgc agtccatcct ctcggatgcc   1560
tggttccact ttgtcttttt tatccaagct gtgcttgtga tactgtctgt cttcttgtac   1620
ttgtttgcct acaaagagta cctcgccctg ctcgtgctgg ccatggccct gggctgggcg   1680
aacatgctct actatacgcg gggttttcag tccatgggca tgtacagcgt catgatccag   1740
aaggtcattt tgcatgatgt tctgaagttc ttgtttgtat atatcgtgtt tttgcttgga   1800
tttggagtag ccttggcctc gctgatcgag aagtgtccca agacaacaa ggactgcagc   1860 tcctacggca gcttcagcga cgcagtgctg gaactcttca agctcaccat aggcctgggt   1920
gacctgaaca tccagcagaa ctccaagtat cccattctct ttctgttcct gctcatcacc   1980
```

-continued

| | |
|---|---|
| tatgtcatcc tcacctttgt tctcctcctc aacatgctca ttgctctgat gggcgagact | 2040 |
| gtggagaacg tctccaagga gagcgaacgc atctggcgcc tgcagagagc caggaccatc | 2100 |
| ttggagtttg agaaaatgtt accagaatgg ctgaggagca gattccggat gggagagctg | 2160 |
| tgcaaagtgg ccgaggatga tttccgactg tgtttgcgga tcaatgaggt gaagtggact | 2220 |
| gaatggaaga cgcacgtctc cttccttaac gaagacccgg ggcctgtaag acgaacagat | 2280 |
| ttcaacaaaa tccaagattc ttccaggaac aacagcaaaa ccactctcaa tgcatttgaa | 2340 |
| gaagtcgagg aattcccgga aacctcggtg tag | 2373 |

<210> SEQ ID NO 7
<211> LENGTH: 3869
<212> TYPE: DNA
<213> ORGANISM: Artificial Sequence
<220> FEATURE:
<223> OTHER INFORMATION: Synthetic construct: mTRPM8

<400> SEQUENCE: 7

| | |
|---|---|
| tcctccctcc tccagtgagc taagagacaa gcaggctctt tgaggagaga gaagctcttg | 60 |
| gctgattgag cagctccacg tcctggctgt cccggagctt gatacataga aaagactgac | 120 |
| ctcagataca cagagatcct tctgcttctg tctcccaagt gctgggatca caggcaagat | 180 |
| gtccttcgag ggagccaggc tcagcatgag gagccgcaga aatggtacta tgggcagcac | 240 |
| ccggaccctg tactccagtg tatctcggag cacagacgtg tcctacagtg acagtgattt | 300 |
| ggtgaatttt attcaggcaa attttaaaaa acgagaatgt gtcttcttta ccagagactc | 360 |
| caaggccatg gagaacatat gcaagtgtgg ttatgcccag agccagcaca tcgaaggcac | 420 |
| ccagatcaac caaaatgaga gtggaactaa caaaaaacat accaaggagt ttccaacaga | 480 |
| cgccttcggg acattcagt ttgagactct ggggaagaaa ggcaagtact tacgcttgtc | 540 |
| ctgtgacacc gactctgaaa ctctctacga actgctgacc cagcactggc acctcaaaac | 600 |
| acccaacctg gtcatttcag tgacgggtgg agccaaaaac tttgctttga agccacgcat | 660 |
| gcgcaagatc ttcagcaggc tgatttacat cgcacagtct aaaggtgcgt ggattctcac | 720 |
| tggaggcact cactacggcc tgatgaagta cataggcgag gtggtgagag acaacaccat | 780 |
| cagcaggaac tcagaagaga acatcgtggc cattggcatc gcagcatggg gcatggtctc | 840 |
| caacagggac acctcatca ggagctgtga tgatgaggga cattttttag ctcaatacat | 900 |
| catggatgac tttaccagag accctctata catcctggac aacaaccata cccacctgct | 960 |
| gcttgtggac aacggttgtc atggacaccc cacagtggaa gccaagctcc ggaatcagct | 1020 |
| ggaaaagtac atctctgagc gcaccagtca agattccaac tatggtggta agatcccat | 1080 |
| cgtgtgtttt gcccaaggag gtggaagaga gactctaaaa gccatcaaca cctctgtcaa | 1140 |
| aagcaagatc ccttgtgtgg tggtggaagg ctcggggcag attgctgatg tgatcgccag | 1200 |
| cctggtggag gtgaggatg ttttaaccte ttccatggtc aaagagaagc tggtacgctt | 1260 |
| tttaccacgc actgtgtccc ggctgcctga agaggaaatt gagagctgga tcaaatggct | 1320 |
| caaagaaatt cttgagagtt ctcacctact cacagtaatt aagatggaag aggctggaga | 1380 |
| tgagattgtg agcaacgcca tttcctatgc gctgtacaaa gccttcagca ctaatgagca | 1440 |
| agacaaggac aactggaatg gacagctgaa gcttctgctg gagtggaacc agttggacct | 1500 |
| tgccagtgat gagatcttca ccaatgatcg ccgctgggag tctgccgacc ttcaggaggt | 1560 |
| catgttcacg gctctcataa aggacagacc caagtttgtc cgcctctttc tggagaatgg | 1620 |
| cctgaatctg cagaagtttc tcaccaatga agtcctcaca gagctcttct ccacccactt | 1680 |

```
cagcacccta gtgtaccgga atctgcagat cgccaagaac tcctacaatg acgcactcct    1740 caccttttgtc tggaagttgg tggcaaactt ccgtcgaagc ttctggaaag aggacagaag    1800
cagcagggag gacttggatg tggaactcca tgatgcatct ctcaccaccc ggcacccgct    1860
gcaagctctc ttcatctggg ccattcttca gaacaagaag gaactctcca aggtcatttg    1920
ggagcagacc aaaggctgta ctctggcagc cttgggggcc agcaagcttc tgaagaccct    1980
ggccaaagtt aagaatgata tcaacgctgc tggggaatcg gaggaactgg ccaatgaata    2040
tgagacccga gcagtggagt tgttcaccga gtgttacagc aatgatgaag acttggcaga    2100
acagctactg gtctactcct gcgaagcctg gggtgggagc aactgtctgg agctggcagt    2160
ggaggctaca gatcagcatt tcatcgctca gcctggggtc cagaatttcc tttctaagca    2220
atggtatgga gagatttccc gagacacgaa gaactggaag attatcctgt gtctattcat    2280
catcccctta gtgggctgtg gcctcgtatc atttaggaag aaacccattg acaagcacaa    2340
gaagctgctg tggtactatg tggccttctt cacgtcgccc ttcgtggtct tctcctggaa    2400
cgtggtcttc tacatcgcct tcctcctgct gtttgcctat gtgctgctca tggacttcca    2460
ctcagtgcca cacacccccg agctgatcct ctacgccctg gtcttcgtcc tcttctgtga    2520
tgaagtgagg cagtggtaca tgaacggagt gaattatttc accgacctat ggaacgttat    2580
ggacaccctg ggactcttct acttcatagc gggtattgta ttccggctcc actcttctaa    2640
taaaagctcg ttgtactctg ggcgcgtcat tttctgtctg gattacatta tattcacgct    2700
aaggctcatc cacattttca ccgtcagcag gaacttggga cccaagatta taatgctgca    2760
gcggatgctg atcgacgttt tcttcttcct gttcctcttt gctgtgtgga tggtggcctt    2820
tggcgtggcc agacagggga tcctaaggca aaatgaacag cgctggagat ggatcttccg    2880
ctctgtcatc tatgagccct acctggccat gtttggccag gttcccagtg acgtggatag    2940
taccacatat gacttctccc actgtacctt ctcgggaaat gagtccaagc cactgtgtgt    3000
ggagctggat gagcacaacc tgccccgctt ccctgagtgg atcaccattc cgctggtgtg    3060
catctacatg ctctccacca atatccttct ggtcaacctc ctggtcgcca tgtttggcta    3120
cacggtaggc attgtacagg agaacaacga ccaggtctgg aaattccagc ggtacttcct    3180
ggtgcaggag tactgcaacc gcctaaacat ccccttcccc ttcgttgtct tcgcttattt    3240
ctacatggtg gtgaagaagt gtttcaaatg ctgctgtaaa gagaagaata tggagtctaa    3300
tgcctgctgt ttcagaaatg aggacaatga actttggcg tgggagggtg tcatgaagga    3360
gaattacctt gtcaagatca acacgaaagc caacgacaac tcagaggaga tgaggcatcg    3420
gtttagacaa ctggactcaa agcttaacga cctcaaaagt cttctgaaag agattgctaa    3480
taacatcaag taaggctggc gatgcttgtg gggagaaacc aaatcacaat gaggtcacag    3540
caaccacctg gatgtggagg ctcatgggac actgatggac agtactgcta atgacttcta    3600
aaggagacat tttcaggtcc ctgagcacag ggtggatgac tcttagtcac cctcaagggc    3660
ataggtcagg gagcaaagtg tacagaggac tttacacctg aagagggtg caaaggacca    3720 tgttcttctg tgaaggtgcc tgtgttttct gcatctcaga gccttgtcct gatgctgagg    3780
gattaagtgt tgacactcct ttcccacgac tgtgactctg gccctgattt tatacttata    3840
ctgcaaaaaa aaaaaaaaaa aaaaaaaaa                                      3869
```